(12) United States Patent
Herzog et al.

(10) Patent No.: US 11,779,346 B2
(45) Date of Patent: Oct. 10, 2023

(54) FIBULA BONE MATERIAL REMOVAL AND TRANSFER TEMPLATE

(71) Applicant: KARL LEIBINGER MEDIZINTECHNIK GMBH & CO. KG, Mühlheim (DE)

(72) Inventors: Rebecca Herzog, Mühlheim (DE); Lorenz Gabele, Mühlheim (DE)

(73) Assignee: KARL LEIBINGER MEDIZINTECHNIK GMBH & CO. KG, Mühlheim (DE)

( * ) Notice: Subject to any disclaimer, the term of this patent is extended or adjusted under 35 U.S.C. 154(b) by 662 days.

(21) Appl. No.: 16/652,368

(22) PCT Filed: Oct. 9, 2018

(86) PCT No.: PCT/EP2018/077505
§ 371 (c)(1),
(2) Date: Mar. 30, 2020

(87) PCT Pub. No.: WO2019/072865
PCT Pub. Date: Apr. 18, 2019

(65) Prior Publication Data
US 2020/0315633 A1    Oct. 8, 2020

(30) Foreign Application Priority Data
Oct. 10, 2017   (DE) ............... 10 2017 123 516.7

(51) Int. Cl.
*A61B 17/15*   (2006.01)
*A61F 2/28*   (2006.01)

(52) U.S. Cl.
CPC .......... *A61B 17/152* (2013.01); *A61F 2/2803* (2013.01)

(58) Field of Classification Search
CPC .................................................... A61B 17/152
See application file for complete search history.

(56) References Cited

U.S. PATENT DOCUMENTS 9,317,634 B2 *   4/2016   Davison ............... A61B 17/152
9,381,072 B2    7/2016   Furrer et al.
(Continued)

FOREIGN PATENT DOCUMENTS

CA    3 019 738    11/2017
CN    104736072    6/2015
(Continued)

OTHER PUBLICATIONS

Russian Office Action from Russian Application No. 20200112973 dated Feb. 16, 2022.
(Continued)

*Primary Examiner* — Nicholas W Woodall
(74) *Attorney, Agent, or Firm* — Beyer Law Group LLP

(57) ABSTRACT

The invention relates to a fibula bone-material removal and transfer template (1) having a main part (4) designed for application to a bone region (3), wherein at least one bone separation-tool guide portion (8) can be or is removably attached to the main part (4), and wherein a receiving pocket (10*a*, 10*b*, 11*a*, 11*b*) designed to receive an implant (9) is formed in the main part (4). The invention also relates to an assembly kit comprising the fibula bone-material removal and transfer template (1) and an implant (9).

10 Claims, 21 Drawing Sheets

(56) References Cited

U.S. PATENT DOCUMENTS

Figure 1:
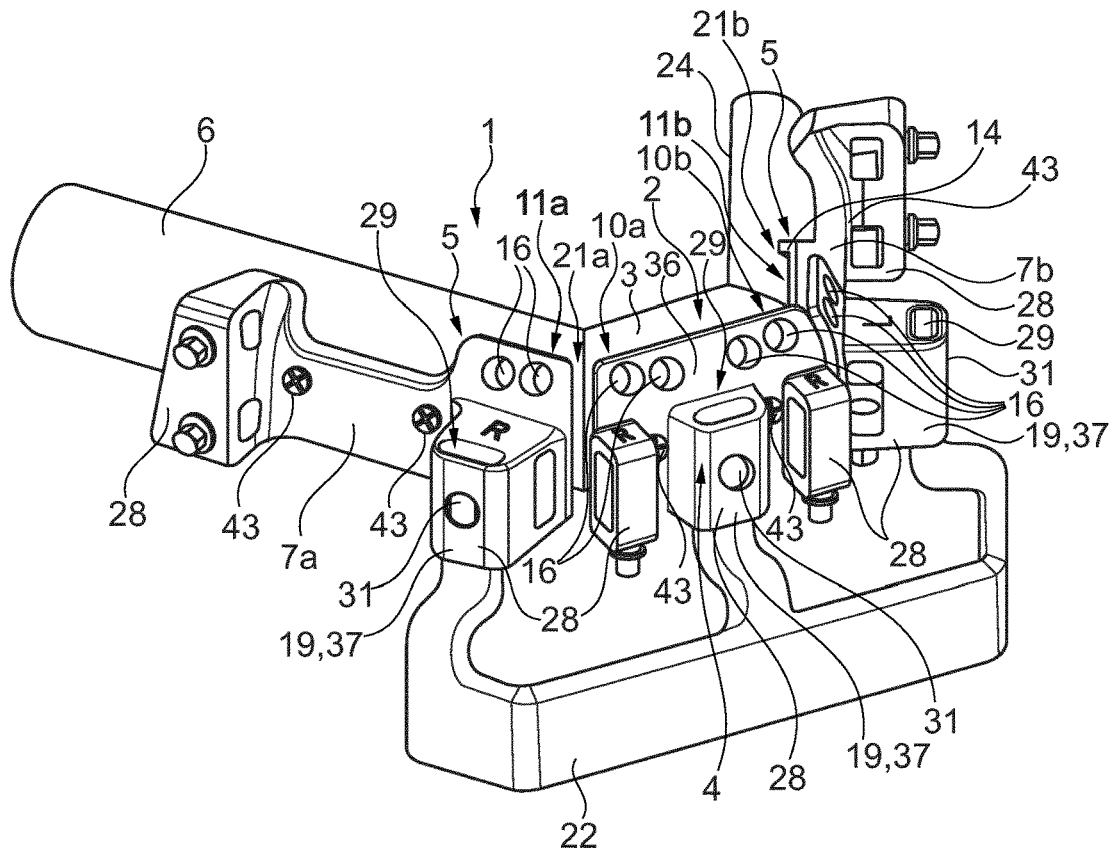

| | | |
|---|---|---|
| 2002/0165552 A1 | 11/2002 | Duffner |
| 2005/0143831 A1 | 6/2005 | Justin et al. |
| 2008/0015605 A1 | 1/2008 | Collazo |
| 2012/0029646 A1 | 2/2012 | Fernandes |
| 2012/0130383 A1 | 5/2012 | Budoff |
| 2012/0209276 A1 | 8/2012 | Schuster |
| 2013/0304075 A1* | 11/2013 | Tseng .................. A61B 17/15 606/102 |
| 2013/0338779 A1 | 12/2013 | Fernandes |
| 2014/0149095 A1 | 5/2014 | Davison et al. |
| 2016/0287298 A1 | 10/2016 | Pavlov et al. |
| 2020/0222060 A1 | 7/2020 | Herzong et al. |

FOREIGN PATENT DOCUMENTS

| | | |
|---|---|---|
| DE | 10 2016 108 433 | 11/2017 |
| EP | 3195816 | 7/2017 |
| JP | 2013-524995 | 6/2013 |
| JP | 2015/517325 | 6/2015 |
| RU | 2269955 | 2/2006 |
| WO | WO 2004/039266 | 5/2004 |
| WO | WO 2011/018458 | 2/2011 |
| WO | WO 2011/136898 | 11/2011 |
| WO | 2013/165558 | 11/2013 |
| WO | 2017/191140 | 5/2017 |
| WO | WO 2017/162444 | 9/2017 |
| WO | WO 2017/191140 | 11/2017 |

OTHER PUBLICATIONS

Indian Office Action from Indian Application No. 202017016660 dated Mar. 8, 2022.

Japanese Office Action dated Jul. 9, 2020 from Japanese Application No. 2020-520584.

German Search Report dated May 18, 2018 from German Application No. 10 2017 123 516.7.

International Search Report dated Jan. 28, 2019 from International Application No. PCT/EP2018/077505.

Chinese Office Action dated Mar. 3, 2023 from Chinese Application No. 201880059856.2.

* cited by examiner

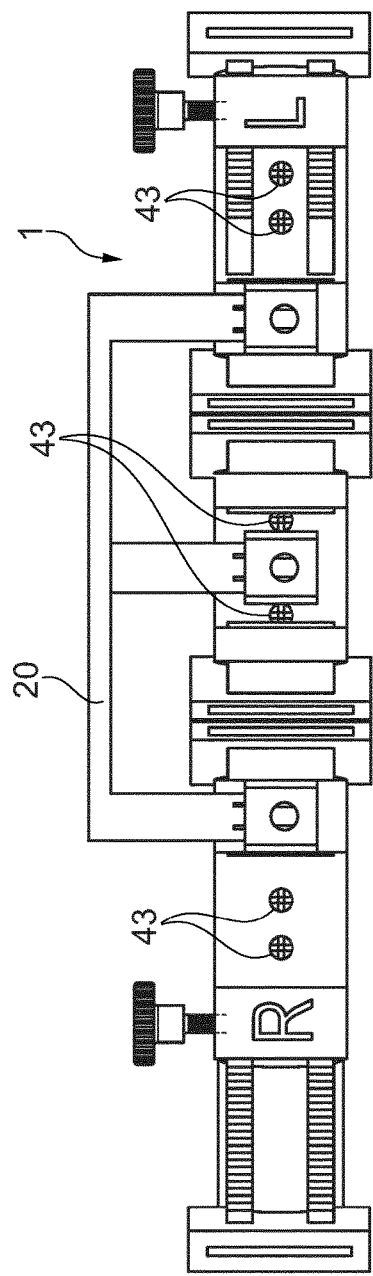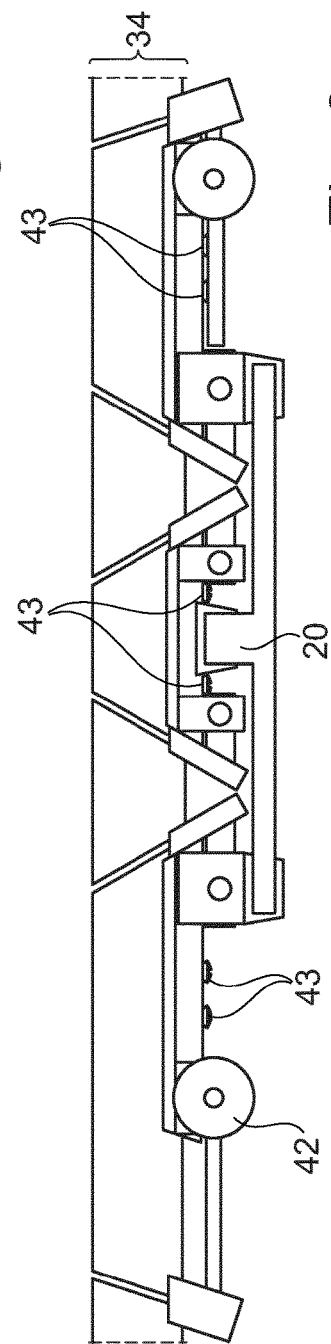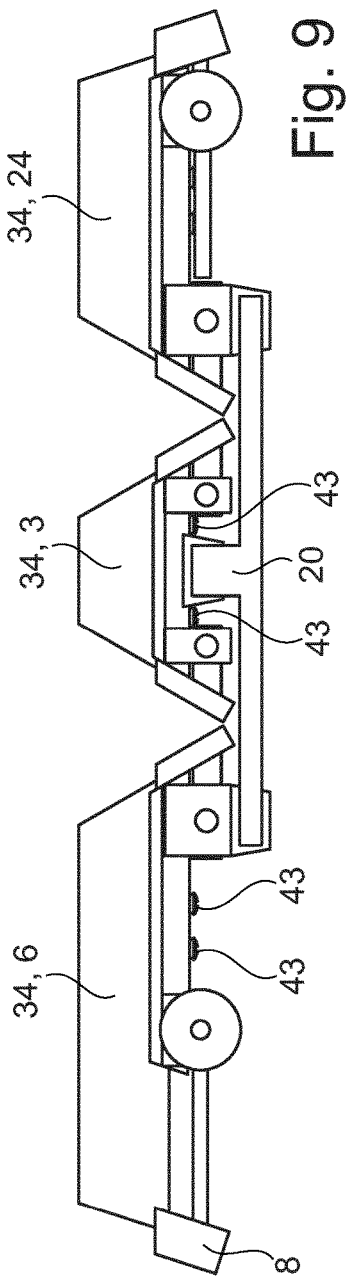

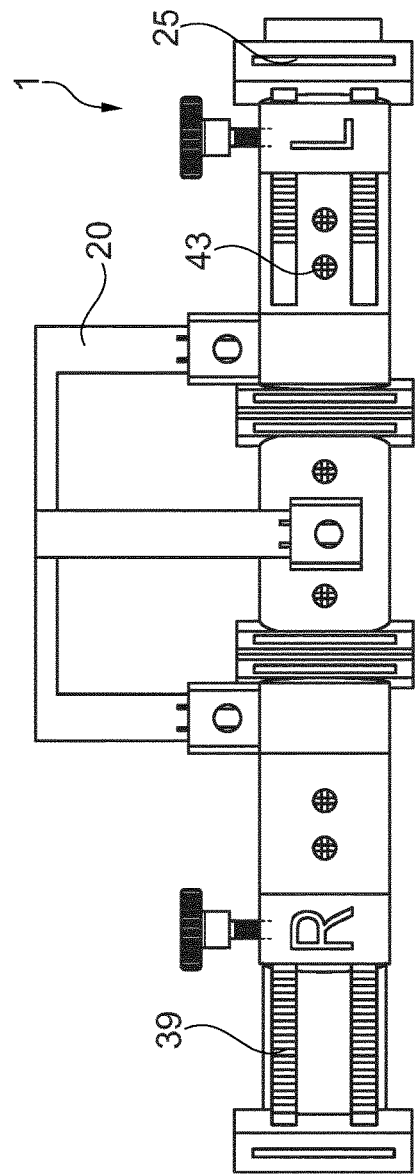
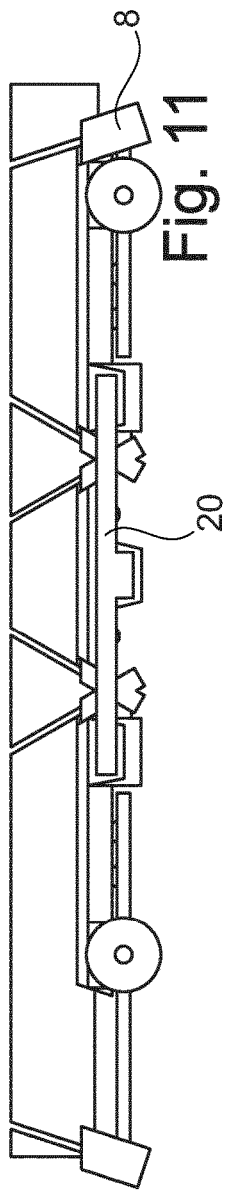
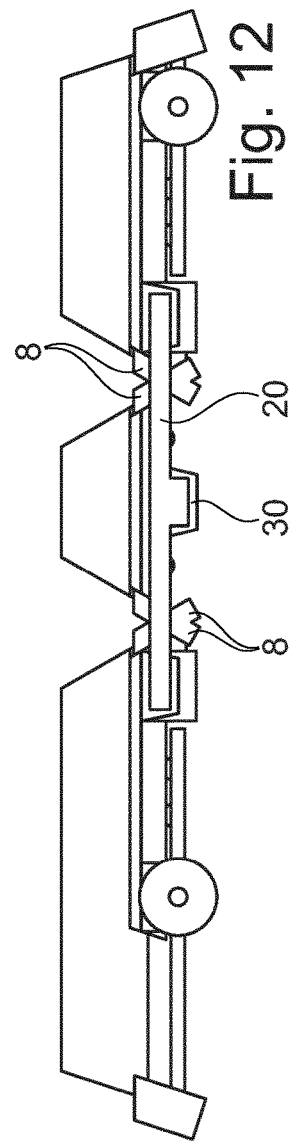
Fig. 10
Fig. 11
Fig. 12

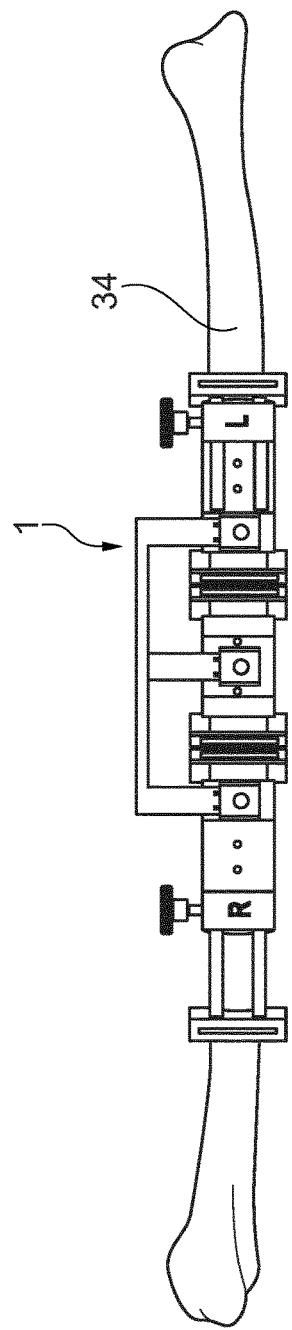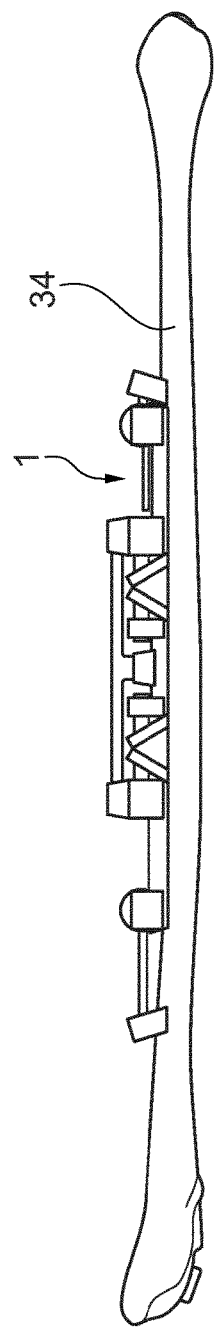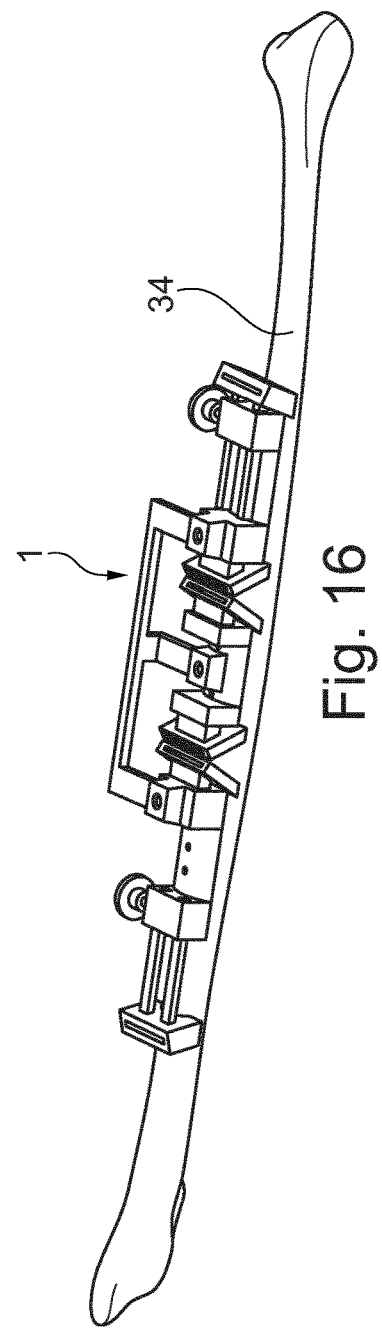

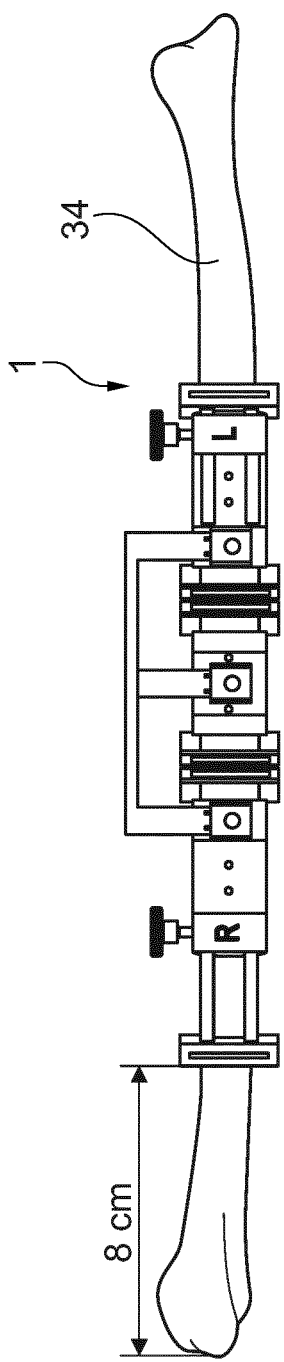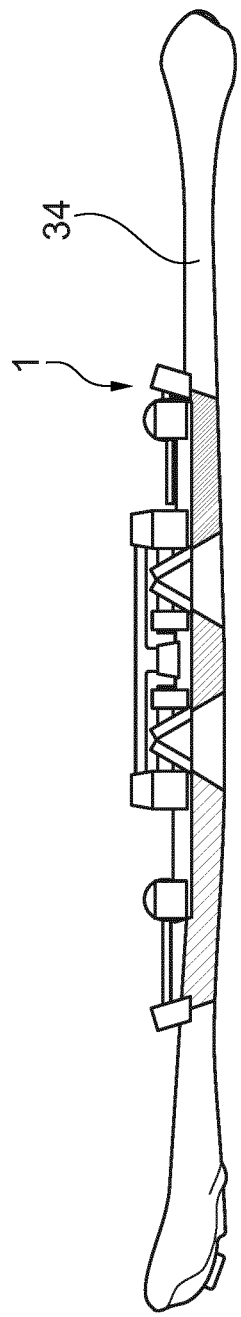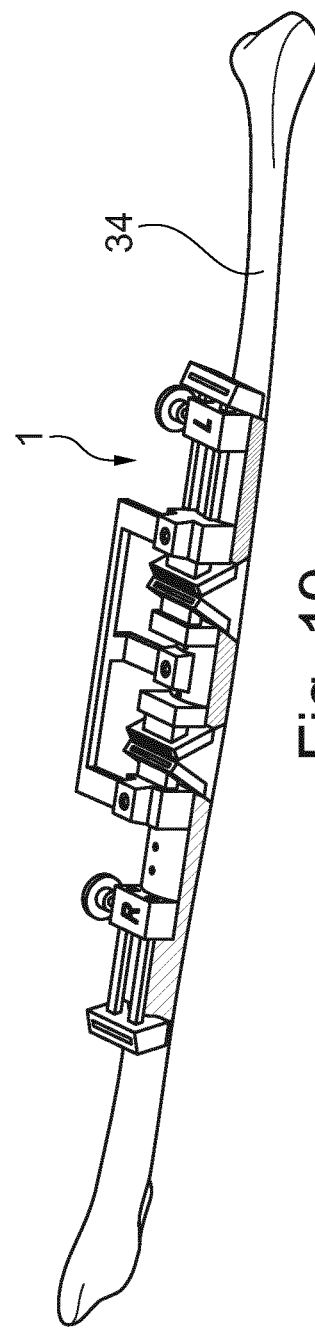

34, 6   34, 3   34, 24

34, 6   34, 3   34, 24

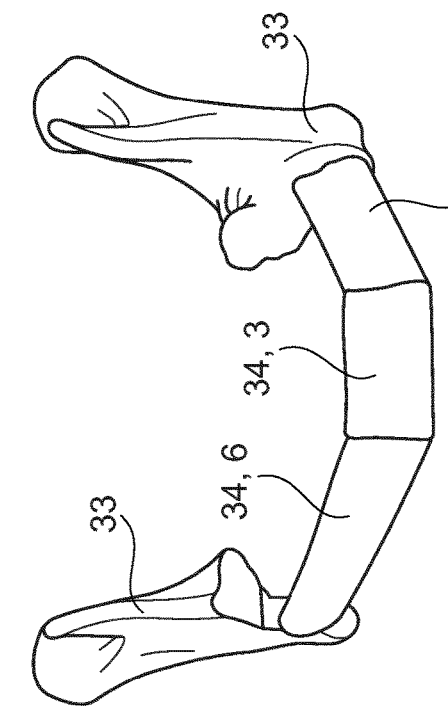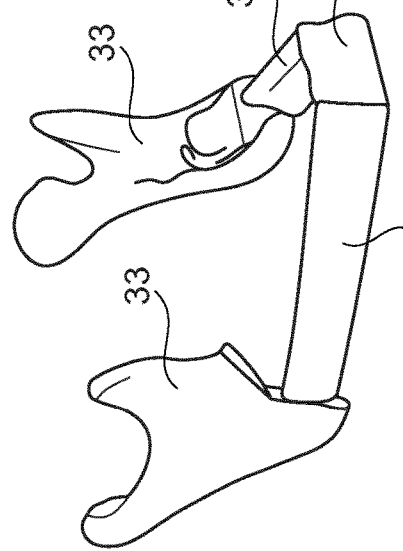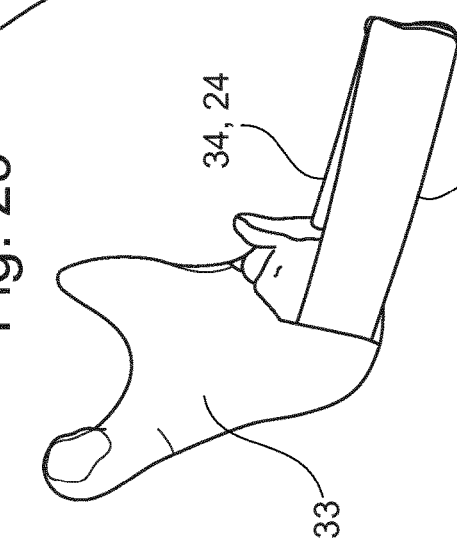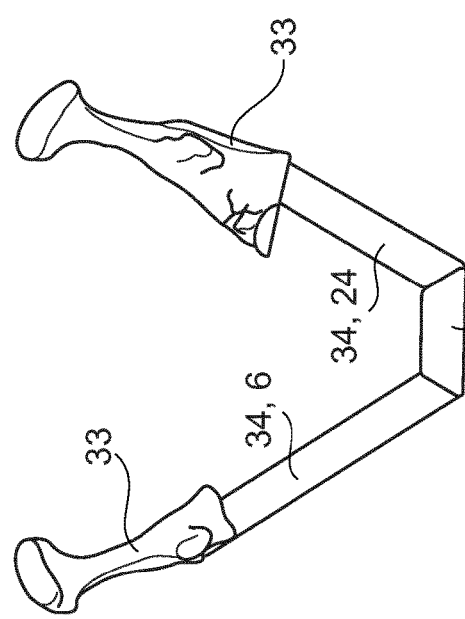

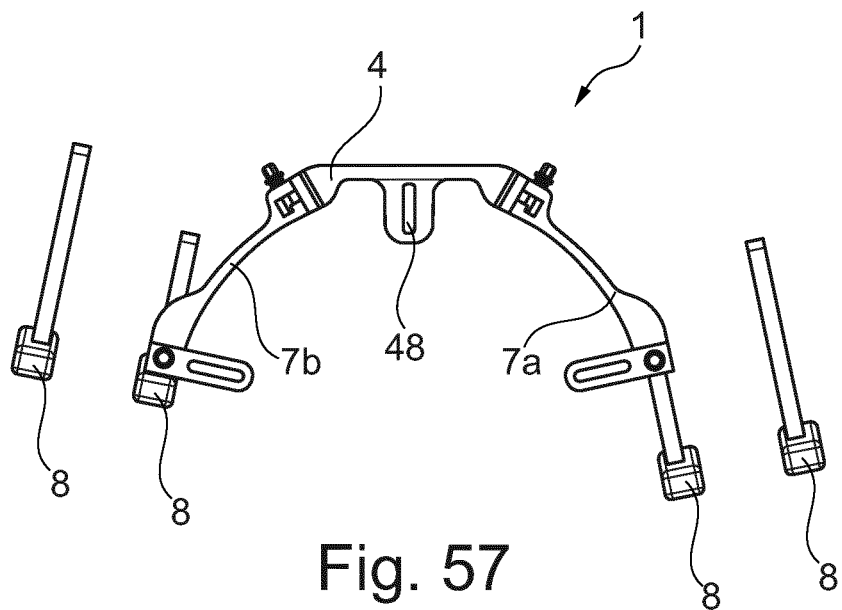
Fig. 57
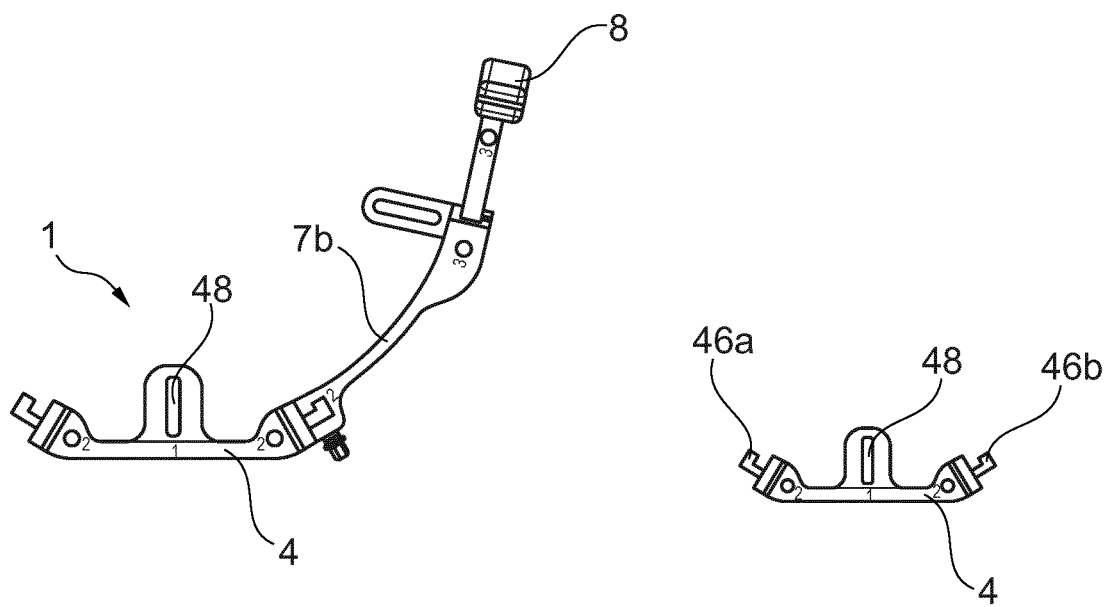
Fig. 58
Fig. 59

FIBULA BONE MATERIAL REMOVAL AND TRANSFER TEMPLATE

The invention relates to a fibula bone-material removal and transfer template, i.e. a template by means of which bone material is removed from a fibula/calf bone and this bone material is transferred in such a way that a specific bone, preferably a lower jaw bone, is reproduced, with a main part designed for application to a bone region, wherein at least one bone separation-tool guide portion can be or is removably attached to the main part. Furthermore, the invention relates to an assembly kit comprising this fibula bone-material removal and transfer template and an implant.

From the prior art, generic templates in the form of sawing templates, such as mandibular resection templates, are already known. WO 2004/039266 A1, for example, discloses a sawing template that can be used on a fibula or a lower jaw bone/mandible. Further prior art is known from US 2012/0029646 A1, US 2013/0338779 A1, US 2013/0304075 A1 and US 2014/0149095 A1.

It happens that human lower jaw bones, for example, are damaged by an accident or carcinogenic changes in such a way that parts of these bones have to be removed. The bone then has to be completed again. Recently, it has been common practice to surgically reinsert bone regions/sections that have been removed from a fibula, for example, back into the area of the lower jaw where the defect has been removed. This requires precise incisions to be made in a predetermined manner both in the lower jaw bone and, correspondingly, in the fibula.

For this purpose, fibula bone-material removal and transfer templates are usually used, which are responsible for precise incision guidance at the lower jaw bone as well as at the fibula and at the same time are used for precise transfer of the excised bone regions for implantation in the jaw area.

However, the solutions known so far are not sufficiently precise, since they are relatively inconvenient to handle. They are also relatively cost-intensive. An improvement is needed here. Another disadvantage of the configurations of the prior art is that the handling of the corresponding templates for performing the surgery is relatively complicated. Especially the positioning of an implant to connect the bone regions used to replicate the lower jaw is relatively complicated.

It is therefore the object of the present invention to overcome the disadvantages known from the prior art and in particular to provide a fibula bone-material removal and transfer template which facilitates handling for the resection of a bone.

This object is solved in a generic fibula bone-material removal and transfer template in that a receiving pocket designed to receive an implant is formed/provided/inserted in the main part.

This significantly simplifies in particular the step of connecting the individual bone regions of the fibula to form the resected bone. All that is needed is to insert the implant into the receiving pocket so that the implant is already positioned at the intended bone regions in the desired position before removing the template. A receiving pocket is in particular understood to be a recess/notch/indentation.

Further advantageous configurations are claimed with the dependent claims and explained in more detail below.

The fibula bone-material removal and transfer template is designed for further applications, if the main part has a first support region for application to a first bone region and, in addition to the main part, a side part is provided which can be or is arranged at the side of the main part and has a second support region for application to a second bone region. At least one bone separation-tool guide portion is preferably attachable or attached to the main part and at least one bone separation-tool guide portion is detachably attachable or attached to the side part.

If a respective receiving pocket designed to receive an implant, preferably in the form of a bone plate, is provided/inserted/formed in the main part and the side part, the implant is held particularly stable.

If a receiving pocket of the main part is open on a side facing the side part and/or a receiving pocket of the side part is open on a side facing the main part, insertion of the implant is further facilitated. It is also possible to choose the design of the implant independently of the shape of the main part/side part.

Furthermore, it is advantageous if the receiving pockets of the main part and of the side part each have an insertion opening for inserting a portion of the implant. The two insertion openings of the two receiving pockets preferably complement each other in such a way that the implant can be inserted in an unhindered manner into a seating space jointly formed by the receiving pockets when the main and side parts are already attached to the bone regions. This further facilitates handling.

It is especially advantageous if the first support region of the main part has a support crosspiece. The height of the support crosspiece of the first support region preferably directly determines the height of the receiving pocket of the main part.

In this respect it is also useful if the second support region of the side part has a support crosspiece. Also the height of the support crosspiece of the second support region then preferably directly determines the height of the receiving pocket of the side part. This keeps the structure of the main part and the side part particularly simple.

In particular, it is advantageous if the support crosspiece of the main part is transverse, especially preferably perpendicular, to a longitudinal axis of the main part and/or the support crosspiece of the side part is transverse, especially preferably perpendicular, to a longitudinal axis of the side part. Furthermore, it is advantageous if the first support region and/or the second support region is/are implemented by a crosspiece/crosspiece region extending multi-dimensionally, preferably by an L-shaped or U-shaped crosspiece.

If the receiving pocket of the main part and/or of the side part has a stop region to support the implant, insertion of the implant is further simplified.

If at least one (first) through hole, opening into the receiving pocket of the main part and penetrating the main part, is inserted in the main part to receive a fixation means, the ease of installation of the implant is further improved.

Therefore it is also advantageous if the side part has at least one through hole, opening into the receiving pocket of the side part and penetrating the side part, to receive a fixation means.

In order to achieve a particularly stable attachment of the implant to the corresponding bone regions, it is advantageous if several through holes, which open into the respective receiving pocket, are provided in the main part and the side part, wherein the through holes of the main part are lined up along an imaginary first connection line and the through holes of the side part are lined up along an imaginary second connection line, which runs/is oriented at an angle to the first connection line and/or to a longitudinal axis of the main part and/or of the side part.

Furthermore, it is advantageous if there is a bracket seating in the main part and/or the side part into/at which an aid bracket connecting the two parts with each other can be plugged in/is plugged in/can be attached/is attached/can be fixed thereto. It is intended to secure the aid bracket to the main part and/or the side part by means of a fixation screw or several fixation screws in the area of this bracket seating.

Furthermore, it is advantageous if the fibula bone-material removal and transfer template has not only one side part but two side parts, wherein a first side part is arranged along a longitudinal axis of the main part towards a first side of the main part and a second side part is arranged along a longitudinal axis of the main part towards a second side of the main part facing away from the first side. The main part, thus implemented as a middle part, and the two side parts then preferably have the receiving pockets for receiving the implant on the sides facing each other.

Preferably, several bone separation-tool guide portions are removably attached to the main part and/or the side part.

It is therefore advantageous if the at least one bone separation-tool guide portion has a guide slit formed between two vertical surfaces, which is open to a front and rear side of the template. In this way, the at least one bone separation tool is prevented from wandering when removing the bone regions from the fibula. A precise removal is thus ensured.

It is further beneficial for handling if the guide slit is open to a lower and/or upper side of the template.

The adjustability and flexibility in use/during surgery is improved if a bar protrudes from the at least one bone separation-tool guide portion separate from the main part and/or side part, which is mounted in a guide portion surrounding it so that it can be moved along its longitudinal axis.

It is also useful if a fixation screw protrudes into the guide portion, which is designed for fixing the bar. A simple change can then be made intraoperatively or can be at least prepared preoperatively.

It is also beneficial for flexible surgical use if both the side part and the main part are equipped with a bone seperation-tool guide portion on the sides facing each other. It is also advantageous if a further bone separation-tool guide portion (preferably slidable and removable from the side part) is arranged on the side of the side part facing away from the main part.

It is also advantageous if the at least one bone separation-tool guide portion of the side part is identical or at least similar to the at least one bone separation-tool guide portion of the main part.

It is then further desirable if the guide slits of two bone separation-tool guide portions attached to the main part enclose a 60° angle +/−5° and the guide slits of two bone separation-tool guide portions attached to the side part enclose an acute angle in the direction of the rear side, approximately a 72° angle +/−5°.

It has proven to be efficient if the bracket seating, preferably in the form of a receiving hole, is arranged approximately in the middle of the main part, wherein an aid bracket, such as a removal-aid bracket or an implant-aid bracket, can be or is inserted into the bracket seating. The receiving hole is further preferably formed by a clamp separate from the main part or a portion of the main part made of a single material. It is also advantageous if the bracket seating, preferably in the form of a receiving hole, is arranged approximately in the middle of the side part, wherein the aid bracket, such as a removal-aid bracket or an implant-aid bracket, can be or is inserted into the bracket seating. The receiving hole is further preferably formed by a clamp separate from the main part or a portion of the main part made of a single material. The individual components of the fibula bone-material removal and transfer template can then be fixed in space so that they cannot be changed relative to each other.

In order to have a better overview of the seating of the aid bracket, the parts (main and side parts) are labeled with 'R' for right and 'L' for left. The use of color markings and/or numerical labels as an alternative or supplement is also considered.

It is also advantageous if the bracket seating of the side part is identical or at least similar to the bracket seating of the main part.

It is advantageous if in the respective bracket seating, the receiving hole is designed in the form of a blind hole or a through hole, wherein the receiving hole is prepared for the locking reception of a spring portion that is fixed to the aid bracket. Quick insertion and removal of the aid bracket is then possible. The spring portion is also omitted in another preferred configuration and the aid bracket is secured in the receiving hole by another fixation means, such as a screw.

It has also proved to be effective if there is a through hole on both sides of the bracket seating for a bone screw and thus for attaching the respective main part or side part.

It is advantageous if the bracket seatings of the main part as well as of the side part are prepared to receive a rigid/stiff/inelastic/form-stable (similar to a steel component) implant-aid bracket. This allows the individual bone regions to be relocated in the exact position.

If the implant-aid bracket is similar to the removal-aid bracket, but differs in the position imposed on the side part and the main part relative to each other, ergo has a different geometrical configuration at the connection points, the bone regions removed from the fibula can be efficiently transferred to the lower jaw bone with its gaps there.

It is also advantageous if the removal-aid bracket forces the side part and the main part into a common plane, but the implant-aid bracket forces the side part and the main part into a U-shape and/or an orientation conforming to the mandibular contour.

The fibula bone-material removal and transfer template is also called fibula resection template and is adapted to the average shape of the fibula. It is therefore not patient-specific, but adapted to the average patient.

In other words, during surgery the individual segments (main and side parts of the template) are connected to each other by means of a removable bracket (aid bracket). The aid bracket can be attached from both above and below to use the template for both the right and left fibula in the same way. In addition, the bracket is provided with a small step in order to protrude further forward, since this area is often obstructed by soft tissue. Furthermore, the removable bracket is designed to be elastic. This means that the individual segments fit snugly to the fibula so that the separation cuts/saw cuts can be made at an exact angle.

The adjustment screws for locking flexible path slots should preferably be mounted orthogonally to the template.

An oscillating saw is to be used to perform the resection. It is intended to design the guide slit/kerf approximately 1.0 mm wide downwards or upwards or open or closed on both sides. Lateral guidance of the saw blade should, however, take place in all cases.

The template is fixed to the fibula with standard screws having an outer diameter of approx. 2.0 mm. In each part (main and side parts) there are two holes (second through holes) for fixation.

Furthermore, the invention relates to an assembly kit of the fibula bone-material removal and transfer template according to the invention according to at least one of the previously described configurations (preferably comprising one of the aid brackets, further preferably comprising both the removal and the implanting-aid bracket) as well as an implant, preferably in the form of a bone plate, wherein the implant is dimensioned such that it can be inserted into a seating space formed by the receiving pocket of the main part.

In the further preferred configuration of the fibula bone-material removal and transfer template with the main part and the at least one side part, the receiving pockets of the facing sides of the main part and of the respective side part together form the seating space, wherein the seating space is then preferably uninterrupted/continuous when viewed along the longitudinal axis of the main part.

The implant is therefore preferably designed with regard to its thickness to correspond to the height or less than the height of the two receiving pockets.

Furthermore, the invention relates to a method for modelling a lower jaw bone from a fibula with the following steps (preferably in chronological order according to the alphabetical sequence):

a) application of the fibula bone-material removal and transfer template according to the invention according to at least one of the previously described configurations with at least the main part and/or a side part on a first bone region of the fibula and optionally with the side part on a second bone region of the fibula, b) cutting the fibula by means of a bone separation tool (preferably formed as a bone saw) guided along the at least one bone separation-tool guide portion in such a way that the two bone regions are separated from each other, c) repositioning of the two separate bone regions in such a way that they are brought into contact and/or into a specific relative position to each other, d) inserting an implant designed to connect the two bone regions, preferably in the form of a bone plate, into the receiving pocket of the main part and/or into the receiving pocket of the side part, and e) fixing the implant by fixation means to the two bone regions under guidance/support of the implant at the main part and/or the side part.

It is further preferable to remove the fibula bone-material removal and transfer template after the implant has been applied, i.e. to separate it from the bone regions, in a further step f) following step e). This further simplifies the resection of the lower jaw bone.

The invention is now explained in more detail below using figures.

Figure 2:
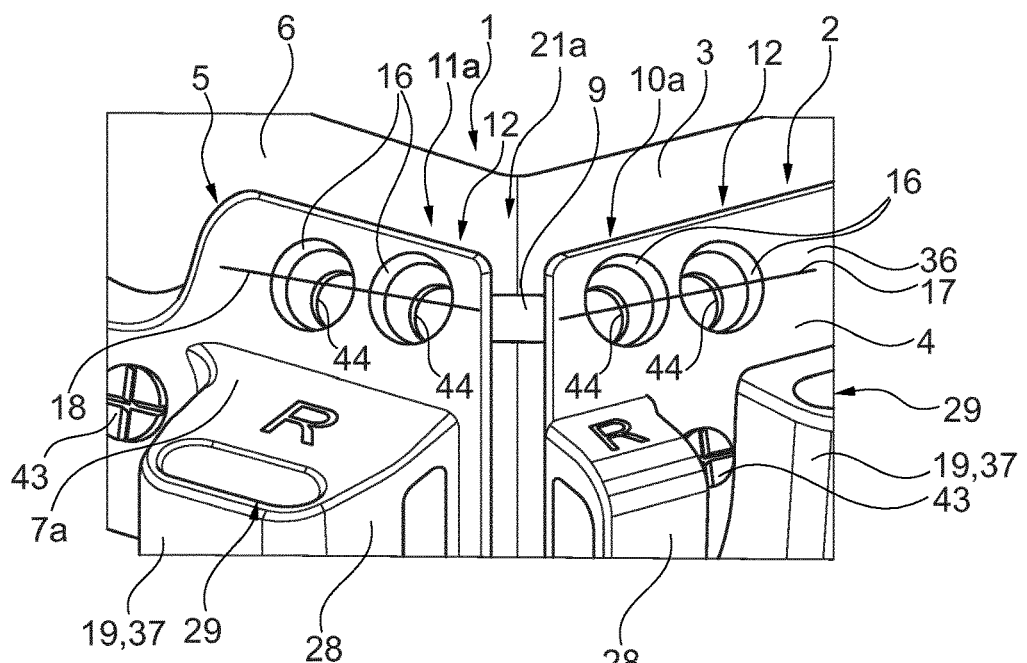
Figure 3:
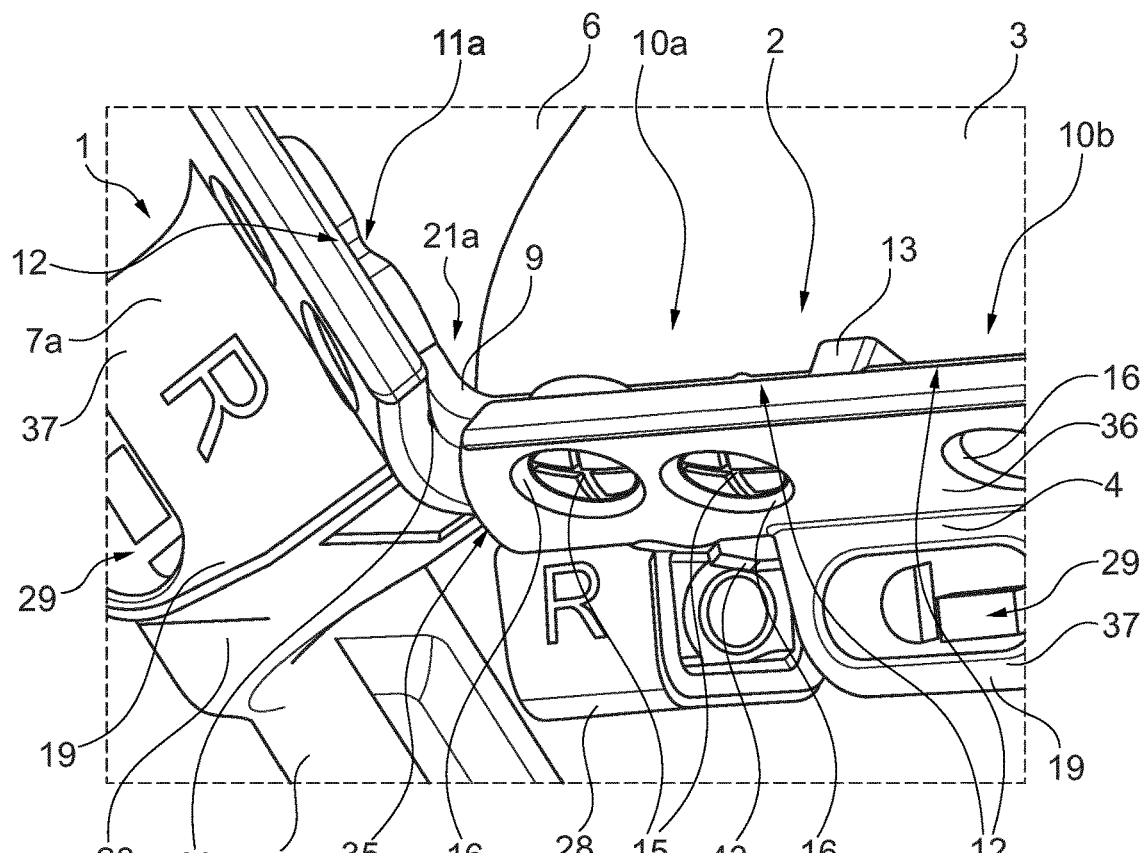
Figure 4:
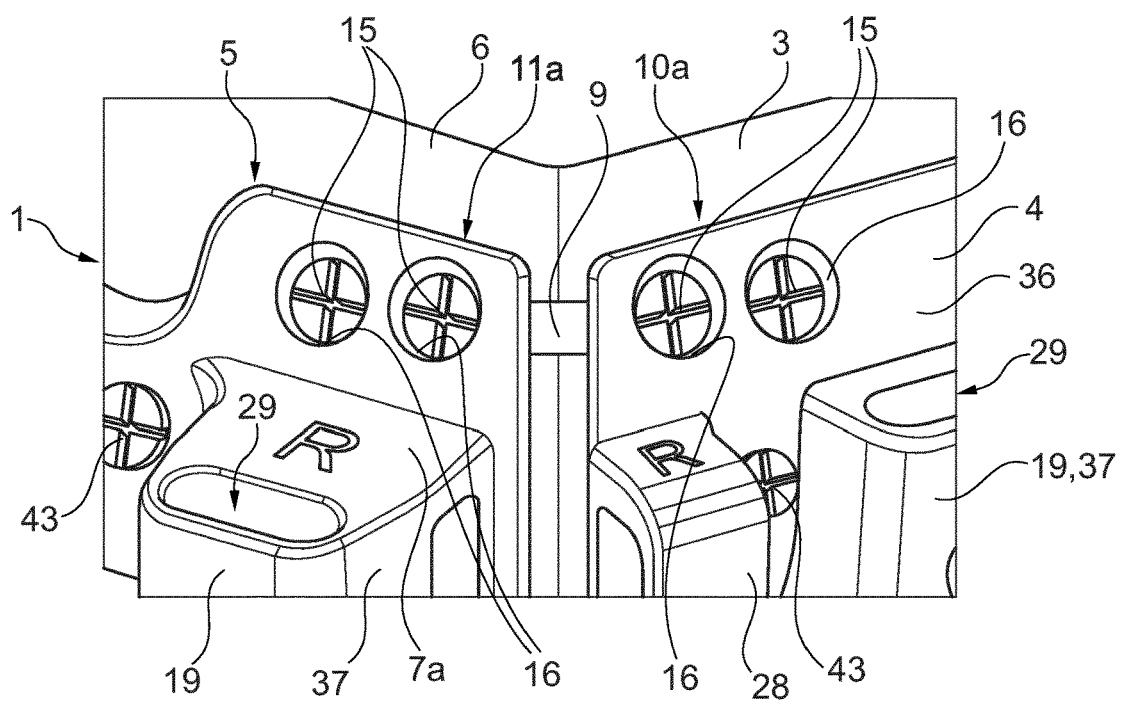
Figure 5:
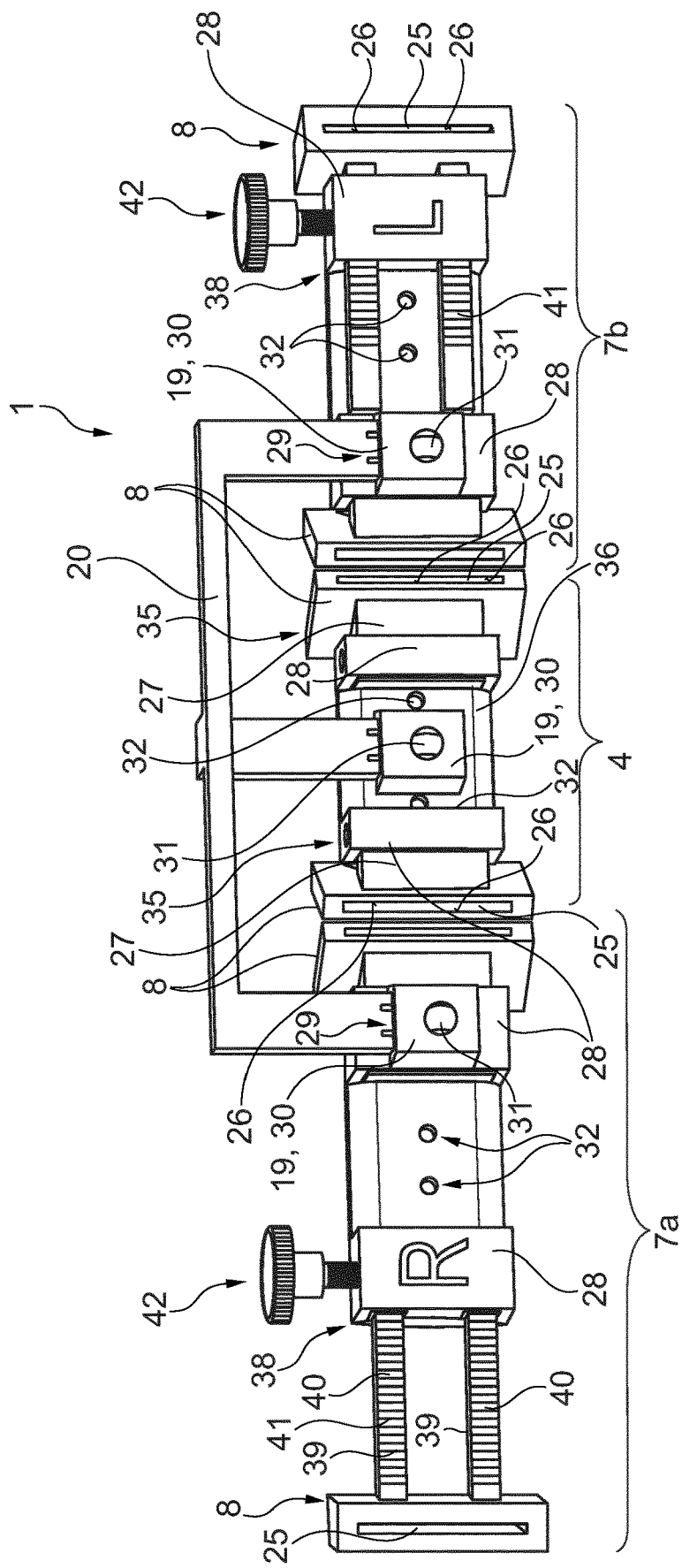
Figure 6:
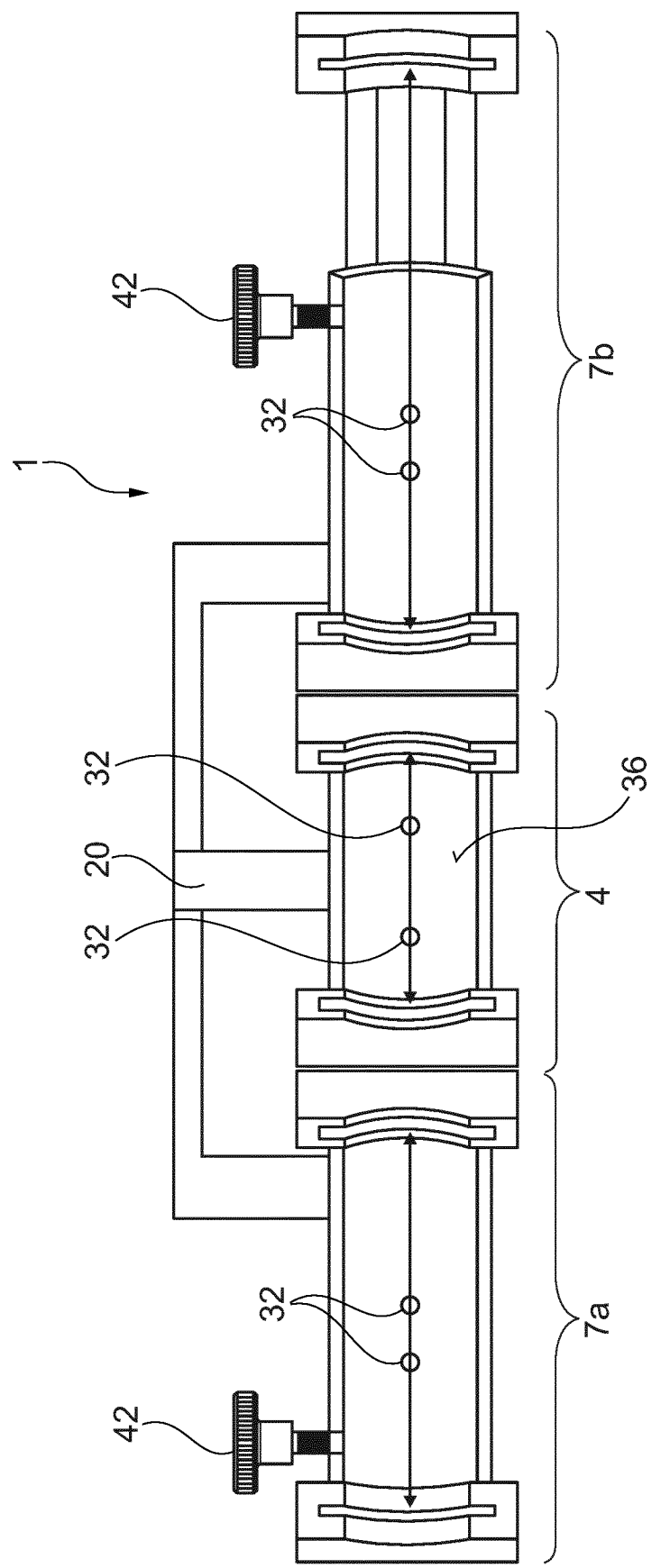
Figure 20:
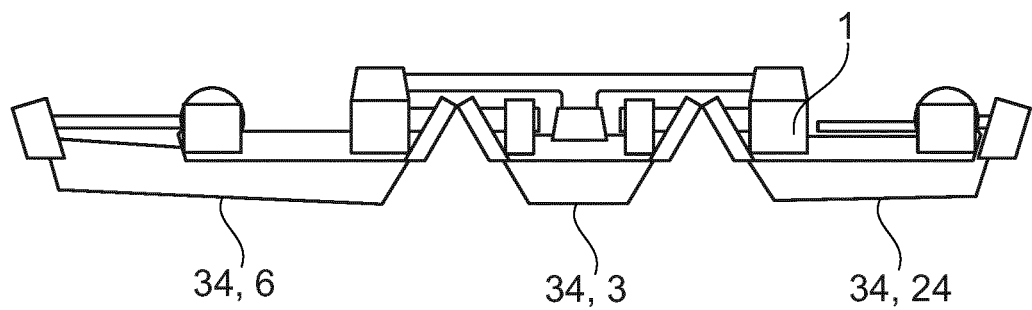
Figure 21:
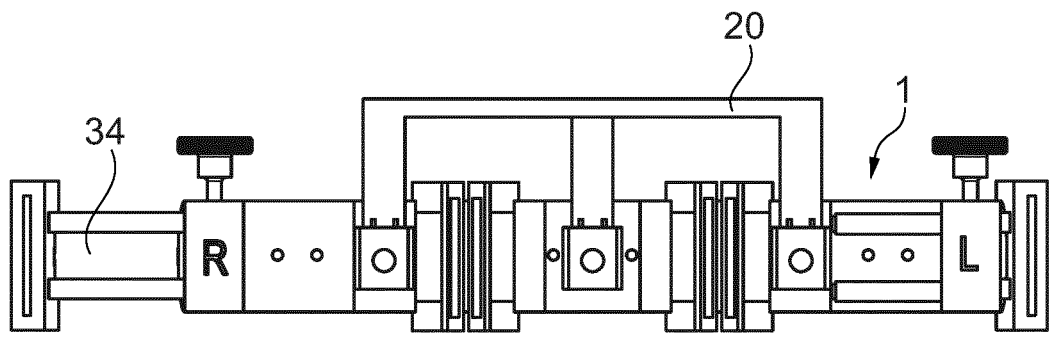
Figure 22:
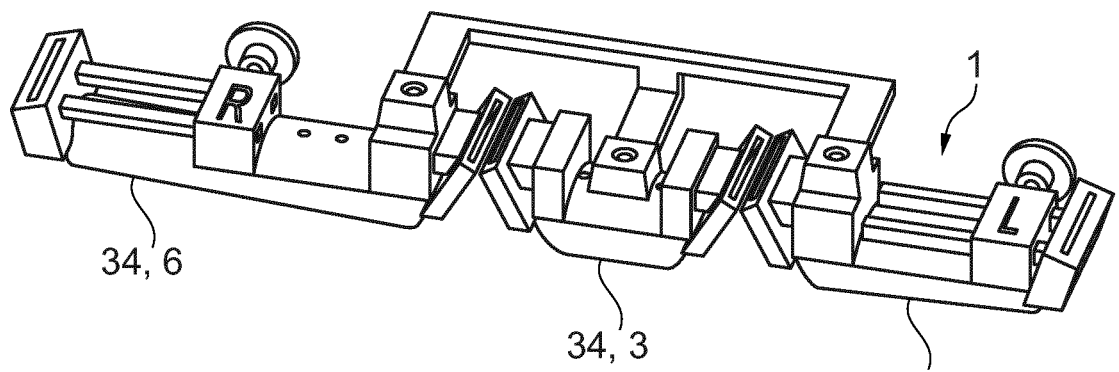
Figure 23:
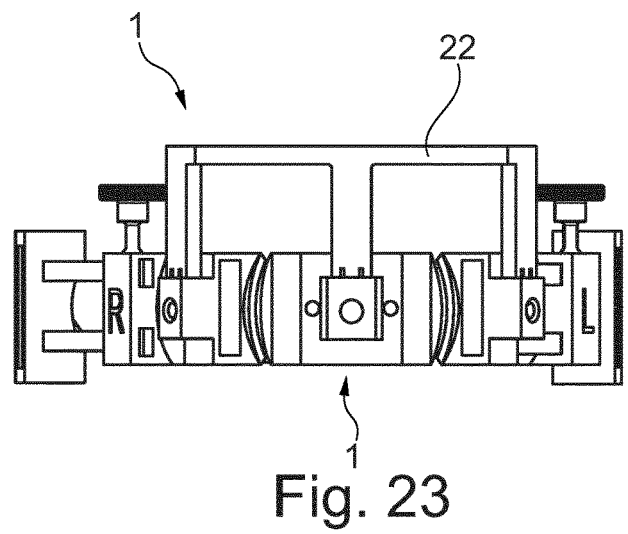
Figure 24:
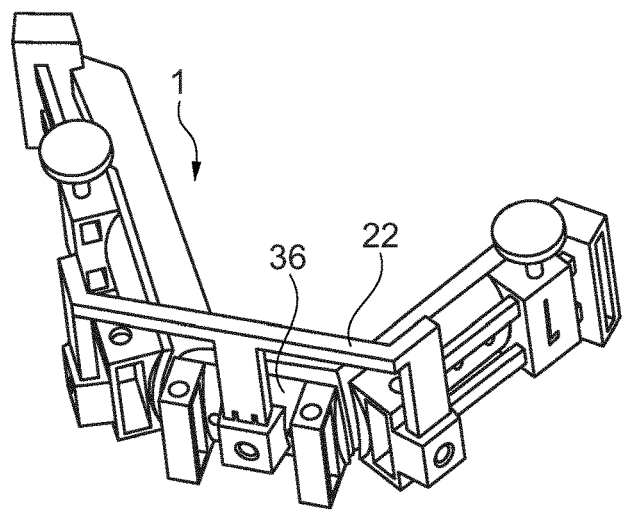
Figure 25:
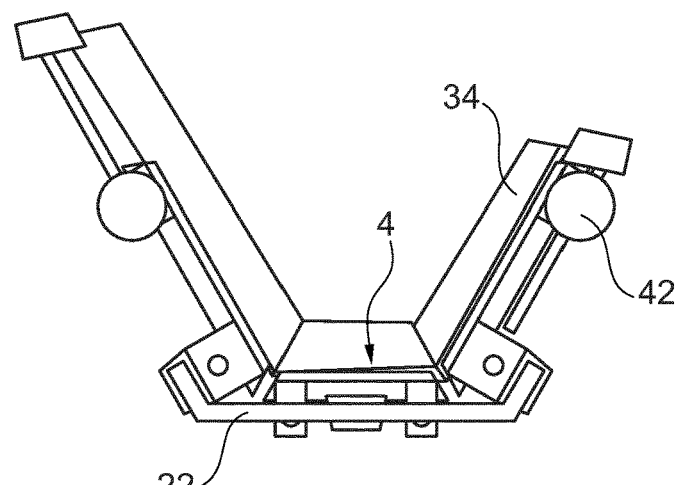
Figure 26:
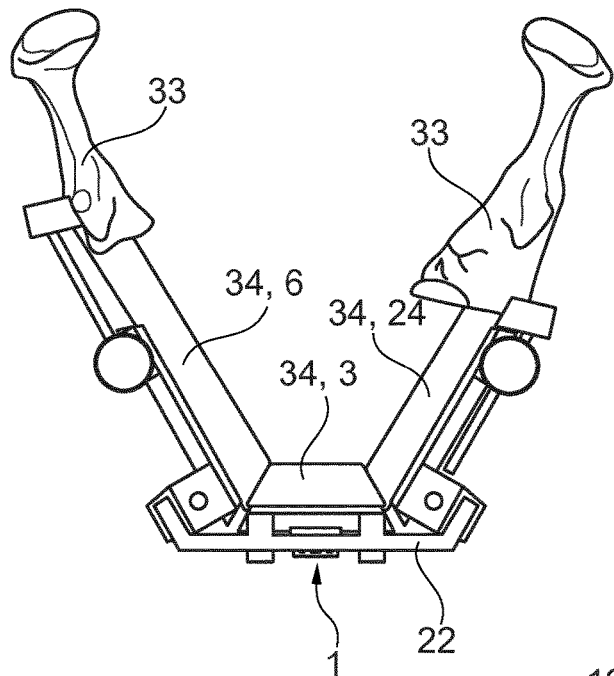
Figure 28:
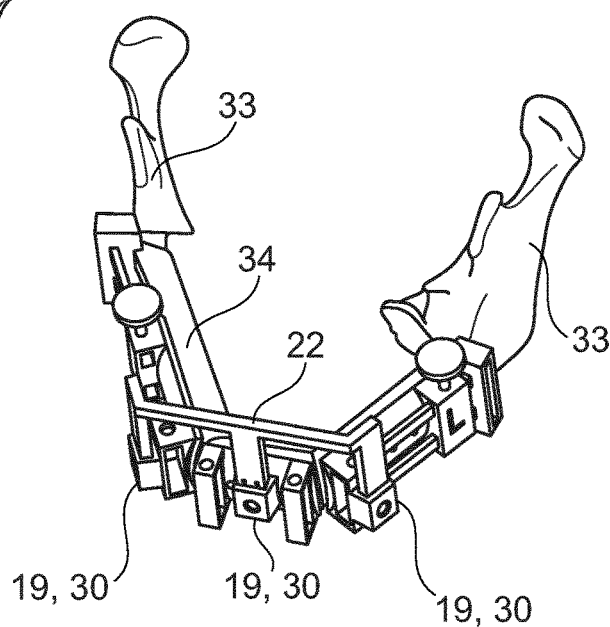
Figure 27:
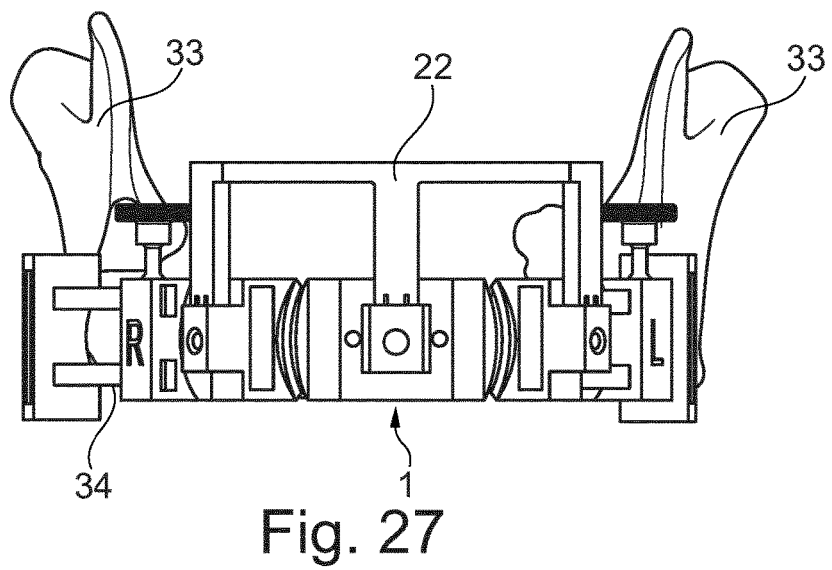
Figure 34:
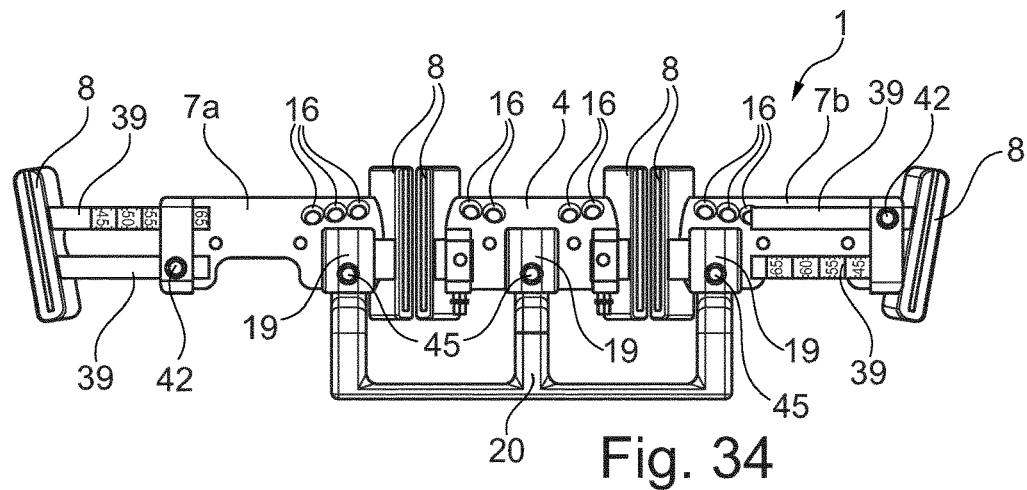
Figure 35:
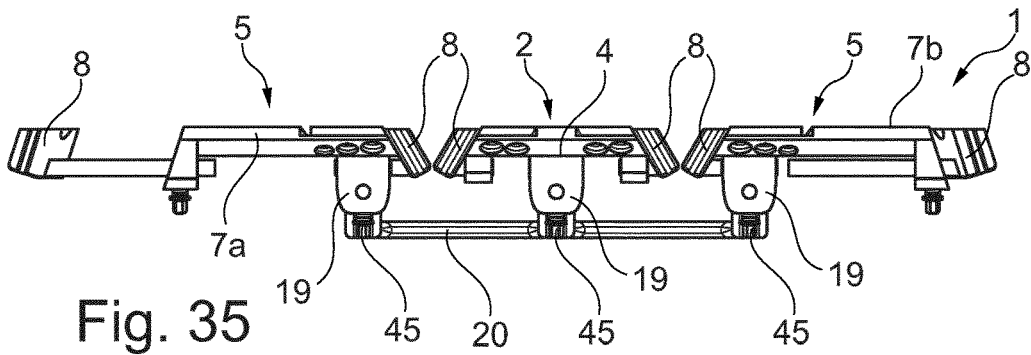
Figure 36:
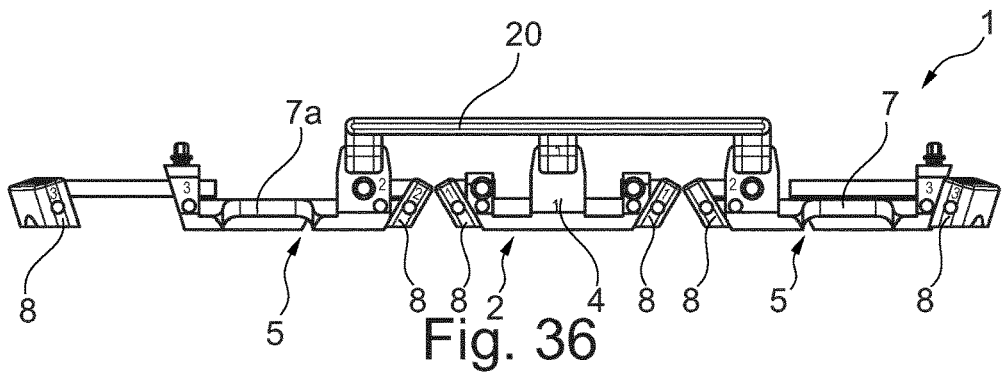
Figure 37:
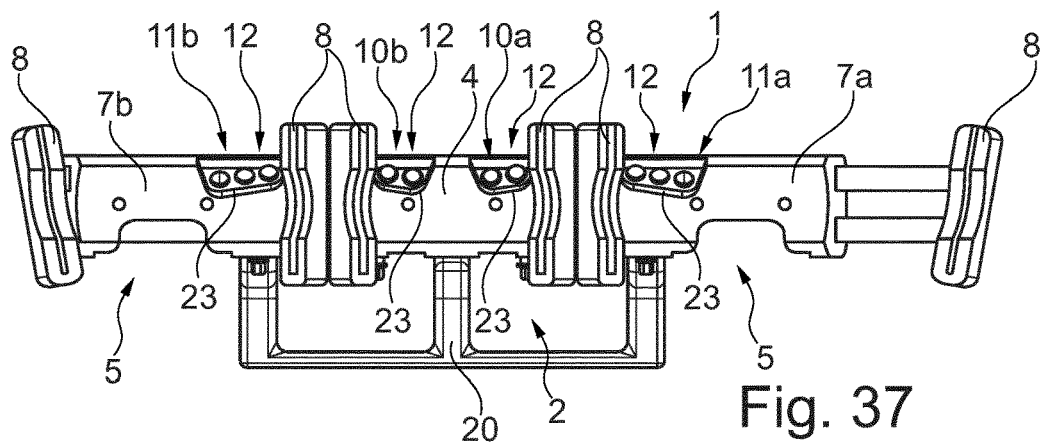
Figure 38:
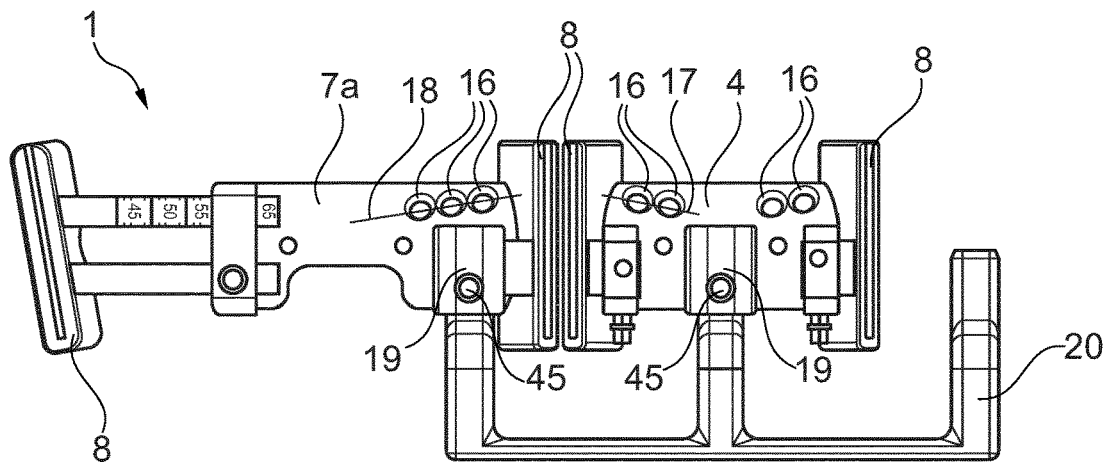
Figure 39:
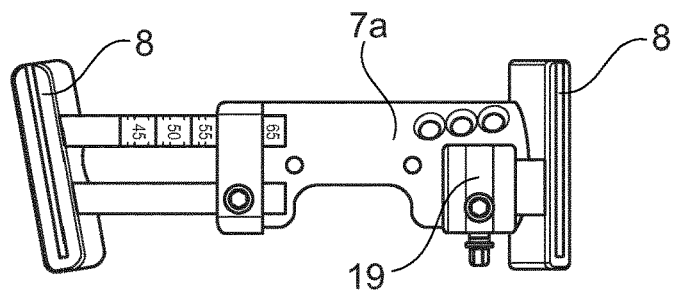
Figure 40:
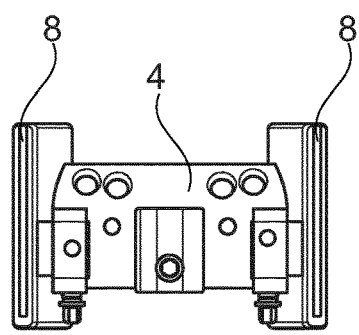
Figure 41:
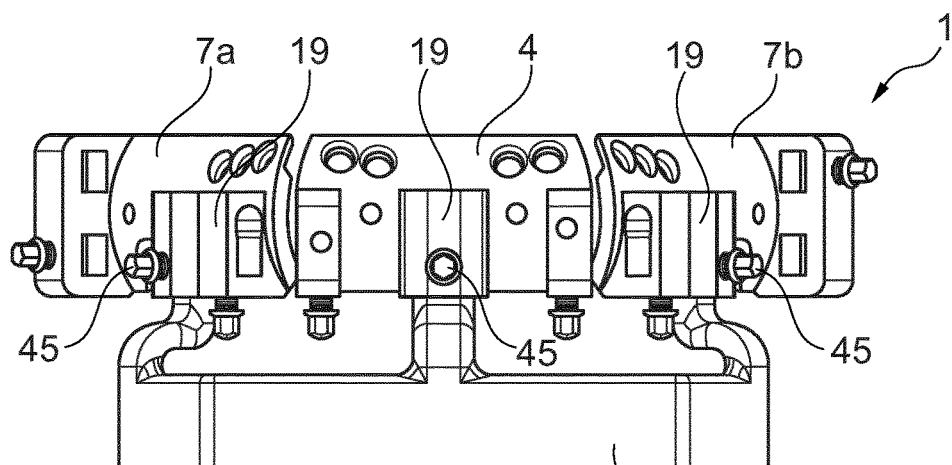
Figure 42:
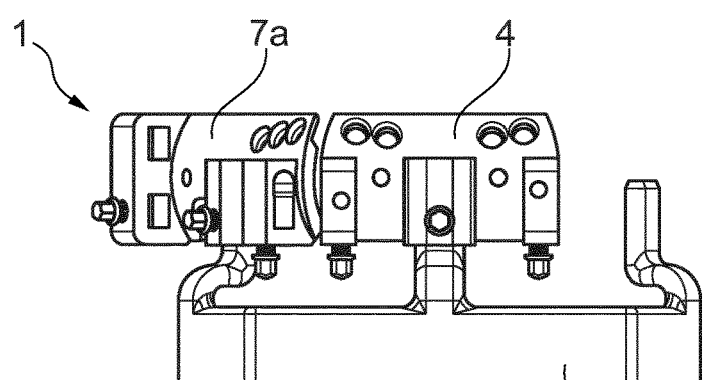
Figure 43:
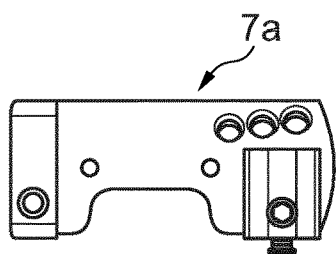
Figure 44:
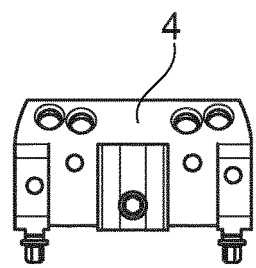
Figure 45:
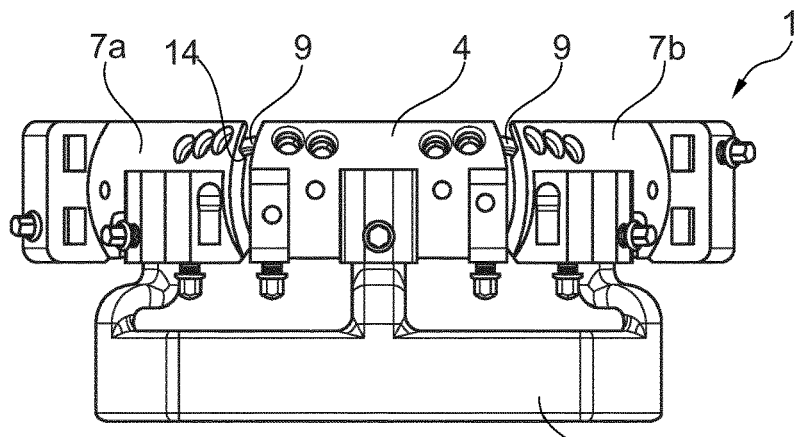
Figure 46:
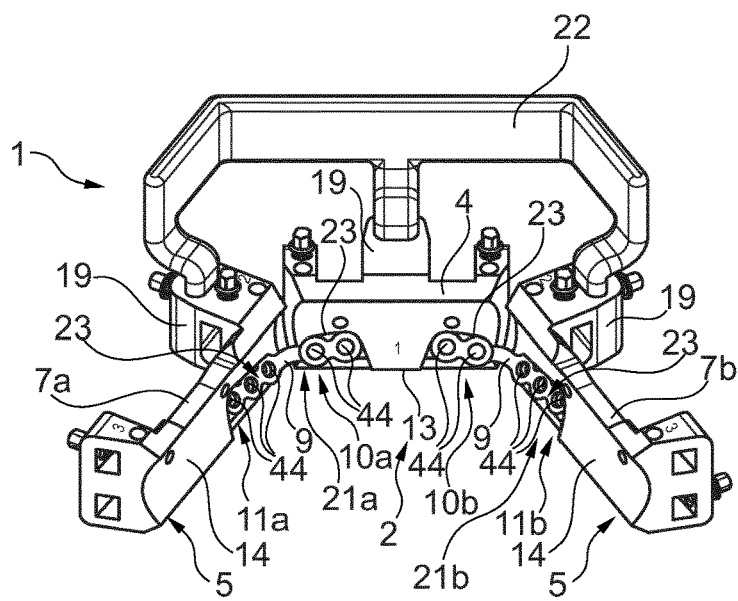
Figure 47:
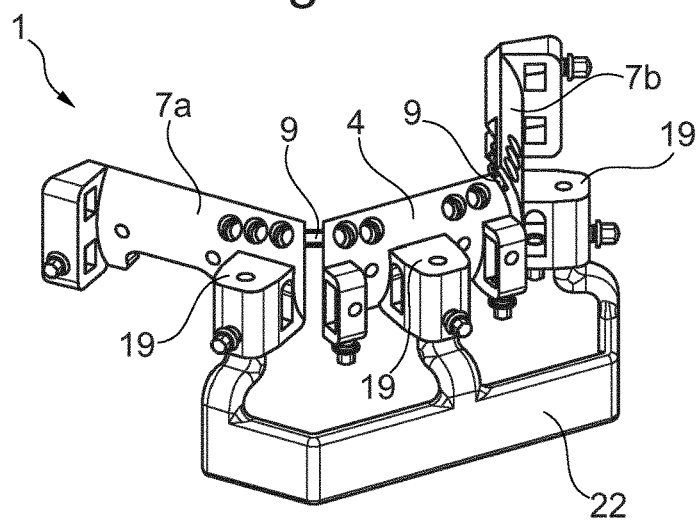
Figure 48:
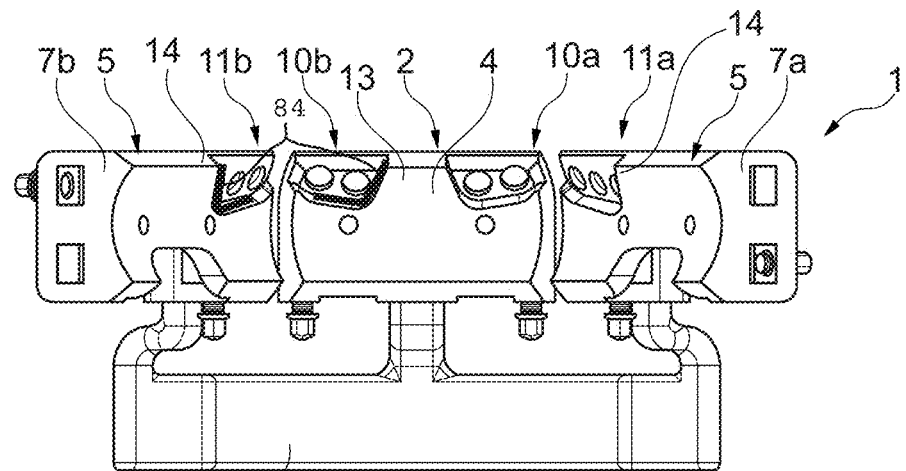
Figure 49:
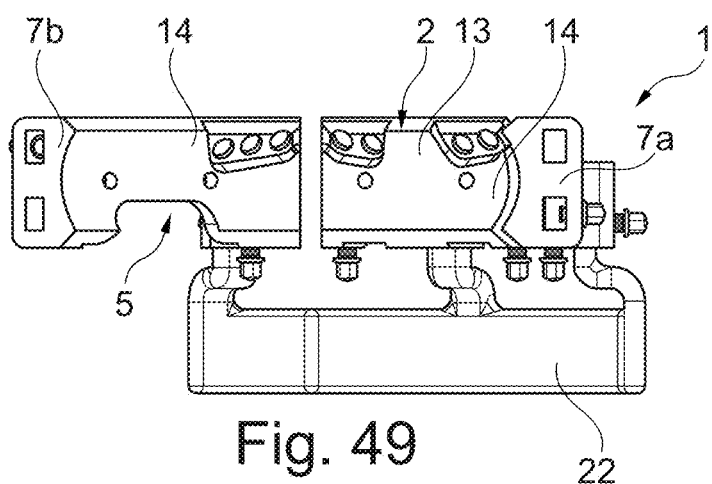
Figure 50:
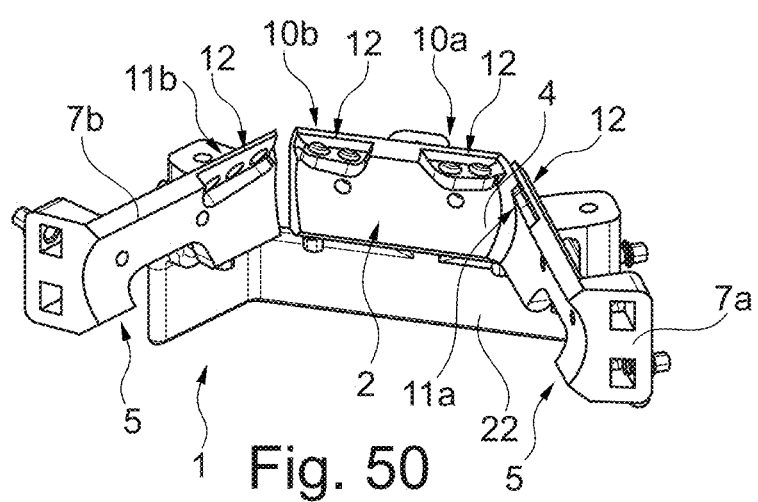
Figure 51:
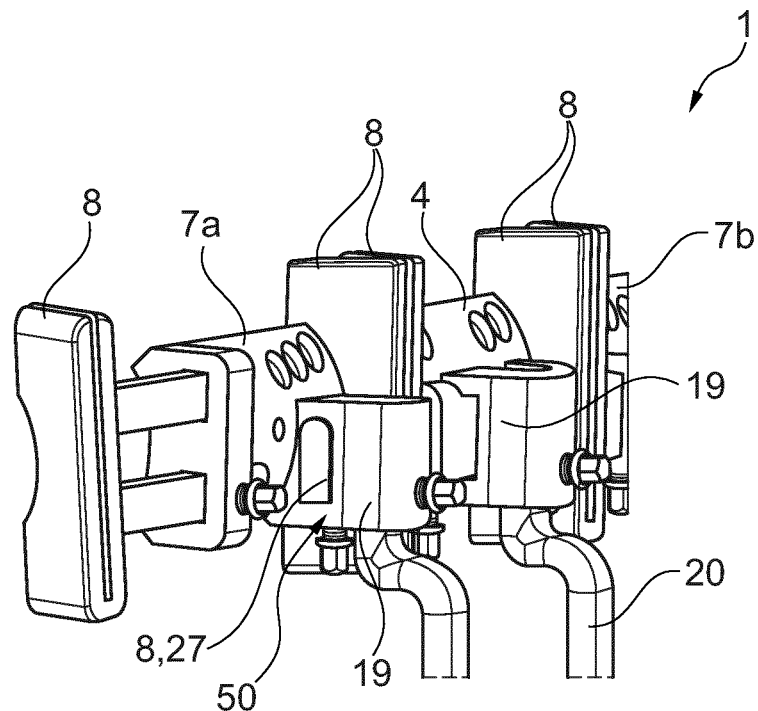
Figure 52:
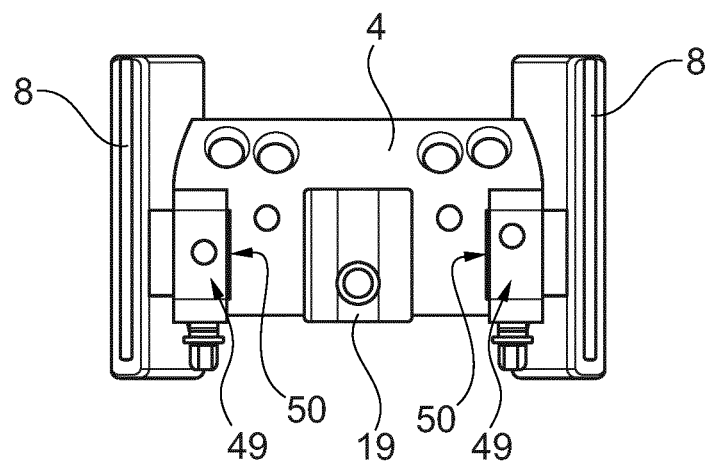
Figure 53:
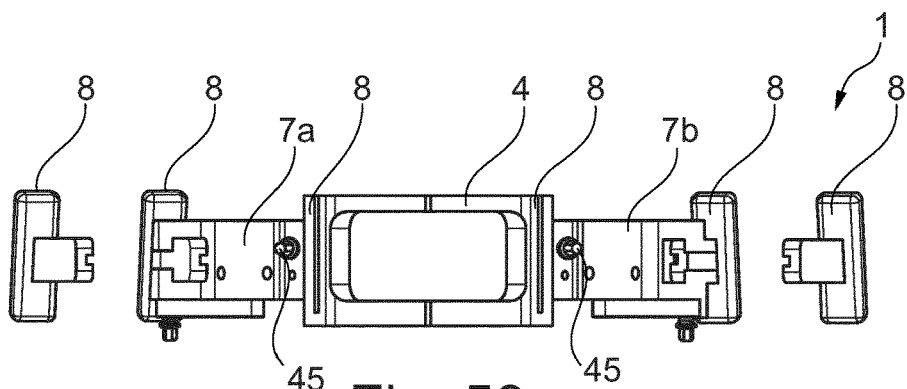
Figure 54:
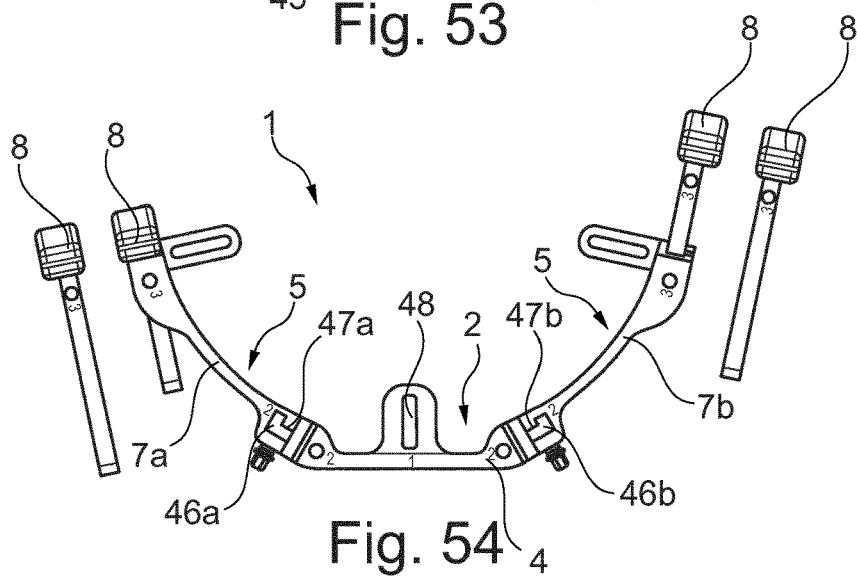
Figure 55:
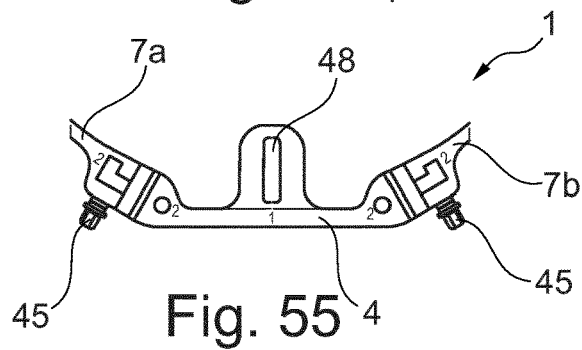
Figure 56:
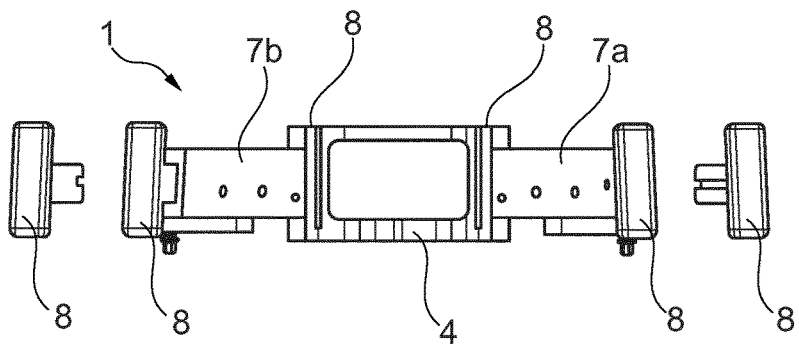

These show:

FIG. 1 shows a perspective view of a fibula bone-material removal and transfer template according to the invention according to a preferred first embodiment, wherein the template is already oriented in an implantation position in such a way that it at least partially reproduces a lower jaw bone in conjunction with the bone regions attached to it, and wherein the individual parts of the template are positioned relative to each other via an aid bracket designed as an implant-aid bracket, FIG. 2 shows a perspective side view of a region between a main part and a first side part of the template according to FIG. 1, wherein a bone plate is inserted in a receiving pocket of the respective part, FIG. 3 shows a perspective view of the area according to FIG. 2 from above, wherein an insertion opening of the respective receiving pocket for insertion of the bone plate is clearly visible and wherein the bone plate is already connected to the bone regions by fixation means, FIG. 4 shows a perspective side view of the region of the template, similar to FIG. 2, wherein the fixation means are again already inserted to attach the bone plate to the bone regions, FIG. 5 shows a perspective view of a front side of a fibula bone-material removal and transfer template according to a configuration comparable to FIGS. 1 to 4, which in particular shows the further structure of the fibula bone-material removal and transfer template according to the invention, but without the formation of the receiving pockets in the main and side parts, FIG. 6 shows the fibula bone-material removal and transfer template of FIG. 5 from a rear side, i.e. from the mandibular side, FIG. 7 shows the fibula bone-material removal and transfer template of FIGS. 5 and 6 from the front side with a low removal-aid bracket, FIG. 8 shows the fibula bone-material removal and transfer template of FIG. 7 from an upper side, wherein the template is already in contact with the fibula and several cuts have already been made in the fibula using bone separation-tool guide portions, FIG. 9 shows the fibula bone-material removal and transfer template of FIG. 8 with removed residual bone sections, wherein the bone regions to be transplanted are attached to the template, FIGS. 10 to 12 show front views of a fibula bone-material removal and transfer template according to a further configuration comparable to FIGS. 1 to 4, wherein a higher removal-aid bracket is used, wherein FIG. 10 corresponds to the representaion in FIG. 7, FIG. 11 to FIG. 8, and FIG. 12 to FIG. 9, FIG. 13 shows the fibula bone-material removal and transfer template of FIGS. 5 to 9 in a transfer/implantation position in which the bone regions to be transplanted are placed in the shape of the lower jaw bone to be replaced or repaired, FIGS. 14 to 16 show further representations of the fibula bone-material removal and transfer template of FIGS. 5 to 9, wherein the template in turn is already in contact with a fibula and wherein FIG. 14 shows a front side, FIG. 15 a bottom side, and FIG. 16 a perspective view, FIGS. 17 to 19 show a further representation of the fibula bone-material removal and transfer template attached to the fibula bone, similar to FIGS. 14 to 16, in several ways of representation, wherein the bone pieces to be removed are marked on the fibula, which is still in one piece, FIGS. 20 to 22 show the fibula bone-material removal and transfer template attached to the fibula in similar ways of representation to FIGS. 17 to 19 with removed bone parts, FIGS. 23 to 25 show the fibula bone-material removal and transfer template of FIGS. 5 to 9 with inserted implant-aid bracket, by means of which the removed bone regions are brought into a shape similar to that of the mandible bone and are thus prepared for transplantation, FIGS. 26 to 28 show the fibula bone-material removal and transfer template of FIGS. 5 to 9 with bone regions placed in position as well as in a state inserted on a residual mandible bone in a view from above (FIG. 26), from the front (FIG. 27), and a perspective view (FIG. 28), FIGS. 29 to 33 show the transplanted bone regions in the lower jaw bone region in different spatial representations (from the top (FIG. 29), from the front (FIG. 30), from the front in perspective (FIG. 31), from the right side in perspective (FIG. 32) and from the left side in perspective (FIG. 33)), FIG. 34 shows a front view of a fibula bone-material removal and transfer template according to the invention according to a preferred second embodiment in the removal position, wherein the template, compared to the first embodiment, has additional fixation screws for securing the respective aid bracket (here the removal-aid bracket), FIG. 35 shows a top view of the fibula bone-material removal and transfer template as shown in FIG. 34, FIG. 36 shows a view of the fibula bone-material removal and transfer template as shown in FIG. 34 from an underside, wherein it can be seen that color and number markings are provided on the main part and the side parts for simplified handling of these parts, FIG. 37 shows a rear view of the fibula bone-material removal and transfer template according to FIG. 34, wherein the receiving pockets formed in the main and side parts are clearly visible, FIG. 38 shows a front view of an assembly of the main part and the first side part of the fibula bone-material removal and transfer template according to FIG. 34, FIG. 39 shows a front view of the first side part of the fibula bone-material removal and transfer template as shown in FIG. 34, FIG. 40 shows a front view of the main part of the fibula bone-material removal and transfer template according to FIG. 34, FIG. 41 shows a front view of the fibula bone-material removal and transfer template of the second embodiment in the implantation position, wherein the bone separation-tool guide portions still attached to the template in the removal position are now removed from the main and side parts, and the side parts are pivoted relative to the main part towards each other, wherein the side parts are secured in a certain angular position relative to the main and side parts by means of an implant-aid bracket, FIG. 42 shows a front view of the assembly of the main part and the first side part of the fibula bone-material removal and transfer template according to FIG. 41, FIG. 43 shows a front view of the first side part used in the fibula bone-material removal and transfer template according to FIG. 41, FIG. 44 shows a front view of the main part used in the fibula bone-material removal and transfer template according to FIG. 41, FIG. 45 shows a front view of the fibula bone-material removal and transfer template according to FIG. 41, similar to FIG. 41, wherein implants in the form of bone plates are already inserted on the side of the receiving pockets, FIG. 46 shows a perspective representation of the fibula bone-material removal and transfer template with the inserted implants according to FIG. 45 from a rear side, wherein the position of the implants in the receiving pockets is clearly visible, FIG. 47 shows a perspective view of the fibula bone-material removal and transfer template according to FIG. 45 from the front side, FIG. 48 shows a rear view of the fibula bone-material removal and transfer template as shown in FIG. 41, wherein the position of the receiving pockets relative to each other is particularly well visible, FIG. 49 shows a rear view of the assembly of main part and second side part of the fibula bone-material removal and transfer template according to FIG. 41, FIG. 50 shows a perspective representation of the fibula bone-material removal and transfer template according to FIG. 41 from the rear side, FIG. 51 shows a perspective side view of the fibula bone-material removal and transfer template of the second embodiment in the removal position as shown in FIG. 34, wherein special milled parts in the bracket seatings are illustrated, FIG. 52 shows a front view of the main part, as used in the fibula bone-material removal and transfer template of FIG. 34, wherein springs attached to the main part in the form of a pin/peg can be seen, FIG. 53 shows a front view of a fibula bone-material removal and transfer template according to a third embodiment according to the invention, wherein the side parts are connected to the main part in a different way as compared to the first embodiment, FIG. 54 shows a top view of the fibula bone-material removal and transfer template as shown in FIG. 53, in which several color and number markings are visible on the main and side parts, FIG. 55 shows a detailed top view of the main part used in the fibula bone-material removal and transfer template of FIG. 53, FIG. 56 shows a rear view of the fibula bone-material removal and transfer template as shown in FIG. 53, FIG. 57 shows a bottom view of the fibula bone-material removal and transfer template according to FIG. 53, FIG. 58 shows a top view of an assembly of the main part and the second side part of the fibula bone-material removal and transfer template according to FIG. 53, and FIG. 59 shows a top view of the main part inserted in the fibula bone-material removal and transfer template of FIG. 53.

The figures are merely schematic in nature and serve exclusively to understand the invention. The same elements are marked with the same reference signs.

FIGS. 1 to 4 illustrate a fibula bone-material removal and transfer template 1 according to the invention (hereinafter referred to as template 1 for the sake of simplicity) according to a preferred first embodiment. The template 1 is already arranged in a state/implantation position that partially reproduces a lower jaw bone.

The complete structure of the fibula bone-material removal and transfer template 1 according to the invention is shown in FIGS. 5 to 38. FIGS. 5 to 28 show a template 1 comparable to the fibula bone-material removal and transfer template of the embodiment according to the invention, which, however, does not explicitly show the receiving pockets 10a, 10b, 11a, 11b, described in more detail below, at its main and side parts 4, 7a, 7b. In the following, the structure and function of the template 1 according to the invention is described on the basis of these comparable template 1 from FIGS. 5 to 38.

The template 1 described in connection with FIGS. 5 to 33 also serves as a fibula bone-material removal and transfer template 1, wherein FIGS. 7 to 33 also show the reconstruction of a lower jaw/lower jaw bone 33 by several bone regions 3, 6, 24/bone parts removed from a fibula/fibula bone 34.

In FIG. 5, a template 1 is shown in a removal position. This template 1 has a main part 4. At a respective (distal) end 35 there is a bone separation-tool guide portion 8 at the main part 4. The bone separation-tool guide portions 8 are designed as jaws/blocks and are detachably connected to a base body 36. In particular, the bone separation-tool guide portions 8 are coupled to the main part 4/base body 36 in a slideable manner. Thus, the main part 4 has a bone separation-tool guide portion 8 at each end 35 along its elongated base body 36 (i.e. along an imaginary longitudinal axis of the main part 4), which is attached in a removable/detachable manner. The two bone-tool guide portions 8 of the main part 4 are thus also mounted so that they can be slid relatively towards and away from each other.

Each bone separation-tool guide portion 8 has a guide slit 25 between two vertical surfaces 26. These guide slits 25 are open/permeable on the front and rear side. Each guide slit 25 is completely surrounded by material except for the elongated openings in the front and rear side. However, a guide slit 25 can be open at the top and/or bottom.

Providing a bar 27 is recommended for allowaing a sliding movement of a bone separation-tool guide portion 8. The bar 27 is mounted in a slidable manner in a guide portion 28 of the main part 4, which encloses it. A fixation screw (not shown here for clarity) can be used to fix the bar 27.

In the middle of the main part 4 there is a bracket seating 19. The bracket seating 29 is formed here as a clamp 30 separate from the base body 36, but is preferably formed in one piece with the base body 36/the main part 4 according to the embodiment of FIGS. 1 to 4. For this purpose, the main part 4 has a receiving hole 29 in the area of elevation 37 (FIG. 1) on base body 36, which also forms the bracket seating 19, and into which an aid bracket can be inserted. In FIG. 5, a removal-aid bracket 20 forming the aid bracket engages with a convex spring portion 31 into the receiving hole 29. Accoridng to other configurations, other fixation means, preferably screws, are also used instead of the spring portion 31 to fix the aid bracket to the bracket seating 19. In FIGS. 1 to 4, however, an implant-aid bracket 22 is inserted in the receiving hole 29.

To the left and right of the clamp 30 there is a respective (second) through hole 32, which penetrates the base body 36 and serves to receive a fixation means in the form of a bone screw. Using the fixation means and through holes 32, it is possible to attach the main part 4 to the fibula bone 34. The through holes 32 are designed in the manner of bores.

A respective side part 7a, 7b is connected to both sides of the main part 4. The main part 4 is therefore also called middle part. The base body 36 of the main part 4 is thus located between the side parts 7a, 7b. Each side part 7a, 7b has two bone separation-tool guide portions 8. A bone separation-tool guide portion 8 of the respective side part 7a, 7b is arranged on a side of the respective side part 7a, 7b facing the main part 4. These bone separation-tool guide portions 8 of the respective side part 7a, 7b are designed the same as the bone separation-tool guide portions 8 of the main part 4. A further bone separation-tool guide portion 8 of the respective side part 7a, 7b is then held on a side of the respective side part 7a, 7b facing away from the main part 4, that is by means of a shifting mechanism 38. Two guide crosspieces 39 are used, both of which have ribs, notches or catches on their front side 40 to form a grating 41.

Bracket seatings 19 in the manner of clamps 30 are again present, in which the ends of the aid bracket/removal-aid bracket 20 engage in FIG. 5. The connection between the removal-aid bracket 20 and the clamps 30 is similar or identical to that already described.

In each of the side parts 7a, 7b there are also (second) through holes 32 to allow attachment to a bone region of the fibula bone 34 via screws. The aid bracket/removal-aid bracket 20 is removable for template fixiation. Adjustment screws 42 are used to fix a flexible path slot in the form of the guide slot 25.

While in FIG. 5 the template 1 is shown essentially from its front side, in FIG. 6 it is shown essentially from its rear side, i.e. viewed from the fibula bone 34. The length of the side parts 7a, 7b should be variable between 45.2 mm or 45 mm and 66.2 mm or 80 mm. The sequence length of the main part 4 should preferably be 30 mm or 34 mm and can be fixed. A rear side of the template 1 is thus prepared for contacting a (human) fibula.

Figure 13:
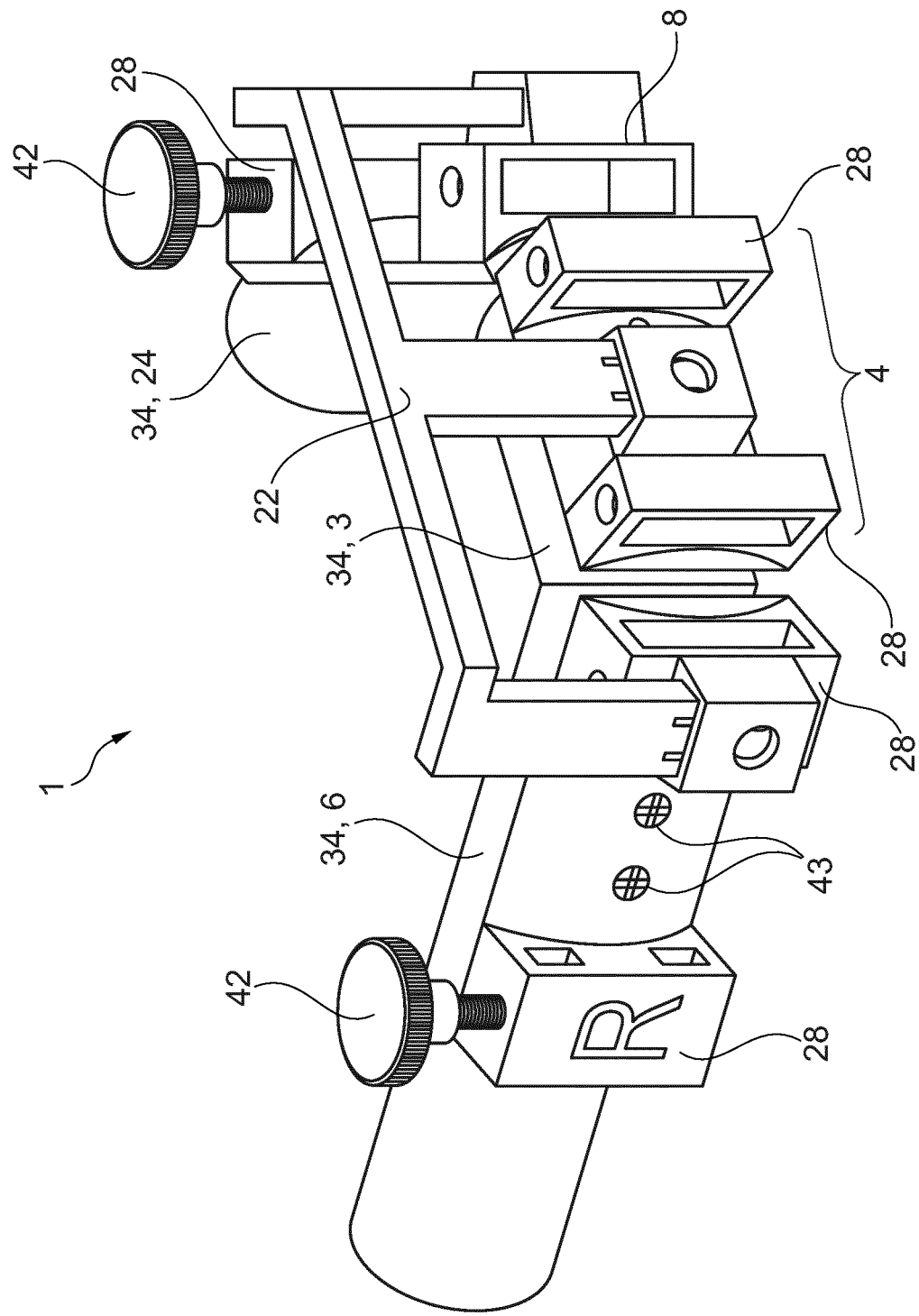

In FIGS. 7 and 10, the fixation means 43 are already inserted in the form of bone screws, in order to achieve fixation to the bone regions 3, 6, 24 of the fibula bone 34, as in FIGS. 8, 9, 11 and 12. In FIG. 13, an implant-aid bracket 22, which is slightly geometrically different from the removal-aid bracket 20, is inserted in a transfer position/implant position of the template 1. The individual cut-off bone regions 3, 6, 24/portions of the fibula bone 34 are then completely rearranged, similar in spatial position to that predefined by the template 1 in connection with the implant-aid bracket 22, preferably identical. The bone separation-tool guide portions 8 have all been removed. The kerfs or respectively guide slits 25 were thus removed in order to be able to place the bone regions 3, 6, 24 "face-to-face".

The process of applying (to the fibula bone 34), cutting (of the fibula bone 34), removal (of the cut-off bone regions 3, 6, 24 of the fibula bone 34) and subsequent assembly (of the bone regions 3, 6, 24 in a form partially reproducing the lower jaw bone 33) is shown in FIGS. 14 to 33.

Coming back to the first embodiment according to the invention of FIGS. 1 to 4, especially with regard to FIG. 1, the overall formation of the template 1 is illustrated in its state attached to the lower jaw bone 33/reproducing the lower jaw bone 33. Accordingly, FIGS. 1 to 4 do not show in particular the bone separation-tool guide portions 8, since these have been removed from the main part 4 and the side parts 7a, 7b.

As indicated in principle in FIG. 1, the main part 4 and the first and second side parts 7a and 7b of the embodiments according to the invention have support regions 2, 5, which serve to attach to the respective bone region 3, 6, 24/to a surface of the bone regions 3, 6, 24.

The main part 4 has a receiving pocket 10a, 10b towards each longitudinal side/each end 35. In particular, the main part 4, which forms an essentially plate-shaped and curved/arched base body 36, has the respective receiving pockets 10a, 10b on a side facing the first bone region 3. The receiving pockets 10a and 10b are thus each open towards the first bone region 3 to which the main part 4 is attached. Furthermore, the receiving pockets 10a, 10b are spatially separated from each other by a (first) support region 2 of the main part 4, as can be seen in FIG. 3. The first support region 2 is arranged in such a way that the respective receiving pocket 10a, 10b is open towards the side part 7a, 7b arranged at the side. The first receiving pocket 10a of the main part 4 is thus opened towards the first side part 7a, whereas the second receiving pocket 10b of the main part 4 is opened towards the second side part 7b. In addition, the receiving pockets 10a, 10b of the main part 4 are open to the surroundings on the top side. The receiving pockets 10a, 10b each form an insertion opening 12, which is dimensioned in such a way that in the state when the template 1 is attached to the fibula bone 24 as shown in FIG. 1, a respective implant 9 in the form of a bone plate can be inserted into the receiving pockets 10a, 10b.

As also shown in FIG. 3, both the first side part 7a (shown here for the first side part 7a) and the second side part 7b also have receiving pockets 11a, 11b. The receiving pockets 11a, 11b of the side parts 7a, 7b correlate with the receiving pockets 10a, 10b of the main part 4. The first side part 7a has its receiving pocket 11a on its (axial) side facing the main part 4, i.e. the first receiving pocket 10a. The second side part 7b has its receiving pocket 11b on its (axial) side facing the main part 4, i.e. the second receiving pocket 10b. The receiving pocket 11a as well as the first receiving pocket 10a are each open on a side facing the other, forming a common, continuous seating space for an implant 9. The receiving pocket 11b as well as the second receiving pocket 10b are each open on a side facing the other, forming a common, continuous seating space for an implant 9. The receiving pockets 11a, 11b of the side parts 7a, 7b are also open on the top side/are provided with an insertion opening 12.

In FIG. 3 it can also be clearly seen that the receiving pockets 10a, 10b, 11a, 11b are each formed by wing-like noses/plate regions on the respective part 4, 7a, 7b. Towards the bottom, the receiving pockets 10a, 10b, 11a, 11b are limited by limit stops/stop regions 23 (in FIG. 3 visible for the receiving pocket 11a of the first side part 7a). The stop regions 23 are formed directly by the respective support region 2, 5 and serve as a support for the implant 9 in its still unattached state relative to the bone regions 3, 6, 24.

The receiving pockets 10a, 10b, 11 a, 11b are already adapted to the shape of the implant (negative to this). The implant 9 is formed by a bone plate bent at an angle of approx. 132° or 120°, but already bent or curved per se. The bone plate is inserted from above into the receiving pockets 10a, 11a or 10b, 11b. Bone plates with a profile/thickness of 1.0 mm, which allow easy implant fixation and are pre-formed up to three-dimensionally on the basis of the average shape of the lower jaw bone 33 or fibula implant 34, have proven to be successful. The contour of the average lower jaw bone 33 and the fibula 34 are generated on the basis of representative data sets. The bone plates 9 are available in different shapes and configurations. The aim is to work with as few bone plates as possible. Preferably, the bone plate, as implemented here, is a four-hole bone plate with a crosspiece. A five or six-hole bone plate with a crosspiece is also possible. The bone plates have multidirectional, angle-stable plate holes 44, in order to be able to provide interlocking fittings as well as to work together with standard screws. Depending on requirements, special instruments such as screwdrivers are used to fix the bone plate in place.

To fix the implants 9, the respective side parts 7a, 7b as well as the main part 4 in the area of the respective receiving pocket 10a, 10, 11a, 11b are provided with (first) through holes 16 in the form of bores which penetrate the main part 4 or the side part 7a, 7b. In particular, the (first) through holes 16 penetrate the wall portion of the main part 4 or the side parts 7a, 7b forming the respective receiving pocket 10a, 10b, 11a, 11b. The wall portion is part of the base body 36 and forms a guide plane for the insertion of the implant 9. The first through holes 16 are dimensioned in such a way that they are designed for the insertion of several fixation means 15 in the form of bone screws for fixing the implant 9 to the corresponding bone region 3, 6, 24. The fixation means 15 are alternatively designed as fixation pins. The fixation means 15 are matched to the first through holes 16 in such a way that they can be pushed through them completely.

After placement of the implants 9 connecting the bone regions 3, 6, 24, the main part 4 and the side parts 7a, 7b are separated from the bone regions 3, 6, 24 by loosening the corresponding previously placed fixation means 43.

FIGS. 2 and 4 also illustrate the arrangement of the (first) through holes 16 in the main part 4 and the first side part 7a. From this it can be seen that the main part 4 has two first through holes 16 at its first receiving pocket 10a, which are lined up with their geometric centers/center axes along an imaginary first connection line 17. The first side part 7a also has two first through holes 16 at its receiving pocket 11a, which are lined up with their geometric centers/center axes along an imaginary second connection line 18. The first connection line 17 runs obliquely to the second connection line 18 and is at an angle between 175° and 150°. The two connection lines 17 and 18 thus form a 'V' standing in space or are skewed to each other. At the second receiving pocket 10b, two additional first through holes 16 are located along a connection line running parallel to the second connection line 18. At the receiving pocket 11b, two additional first through holes 16 are located along a connection line running parallel to the first connection line 17.

In connection with FIGS. 34 to 52, a further second embodiment according to the invention of the fibula bone-material removal and transfer template 1 is shown. This second embodiment is constructed and functions according to the first embodiment, unless described otherwise below.

FIG. 34 clearly shows that fixation screws 45 are screwed into the bracket seatings 19 for additional fixation of the respective aid bracket—here for the removal-aid bracket 20 and in connection with FIGS. 41 and 45 to 51 for the implanting-aid bracket 22. The fixation screws 45 are screwed to a thread of a through hole formed in the bracket seating 19 and act on the aid bracket 20, 22 in a tightened position in such a way that they secure/fix the respective aid bracket 20, 22 relative to the main part 4 and the side parts 7a, 7b. In the main part 4 as well as in the respective side parts 7a, 7b, a respective fixation screw 45 is inserted in the respective bracket seating 19. Preferably, the fixation screws 45 are colored with a specific color, preferably golden. In particular, the fixation screws 45 are colored for better recognition at their blade attachment (i.e. their tool holder contour).

Furthermore, FIG. 34 shows that the bone separation-tool guide portions 8 of the side parts 7a, 7b, which are attached to the side of the respective side part 7a, 7b facing away from the main part 4, as in the first embodiment, are slidably guided in the respective side part 7a, 7b. For this purpose, guide crosspieces 39, which are guided in the respective side part 7a, 7b via a shifting mechanism, are provided on the bone separation-tool guide portions 8 of the side parts 7a, 7b, which are attached to the side of the respective side part 7a, 7b facing away from the main part 4. Each of these bone separation-tool guide portions 8 has two guide crosspieces 39. In addition, a length measurement is indicated/inserted/provided on one of the two guide crosspieces 39 of the respective bone separation-tool guide portion 8, in order to bring the movable bone separation-tool guide portion 8 into the desired position in advance. The movable bone separation-tool guide portion 8 can be fixed with the adjustment screw 42. In addition, the movable bone separation-tool guide portions 8, which are each arranged on a side of the respective side part 7a, 7b facing away from the main part 4, are designed in such a way that they can be exchanged as desired and can therefore be interchanged.

In other words, the position/location of the variable kerf (the movable bone separation-tool guide portion 8) can be determined according to the length of the side segments (length of the guide crosspieces 39). Preferably, length-measurement markings between 45 mm and 65 mm or between 65 mm and 80 mm are provided on the respective guide crosspiece 39. Preferably, the scale values/length-measurement markings are only provided on the guide crosspiece 39 of the total of two guide crosspieces 39 of the bone separation-tool guide portion 8 that does not come into contact with the additional screw (adjustment screw 42). In addition, the variable kerfs/bone separation-tool guide portions 8 are labeled/marked in such a way that the scale with the length measurement is only on the side that is not fixed in the slot with the adjustment screw 42.

In addition, a spring groove guide/seating is preferably provided, forming a form fit with the movable bone separation-tool guide portions 8, which are each arranged on a side of the respective side part 7a, 7b facing away from the main part 4. A groove 50 of the spring groove guide (FIG. 52) formed in the movable bone separation-tool guide portion 8 (preferably by a special milled part) and a spring in the form of a pin 49/peg of the spring groove guide, which is provided on the respective side part 7a, 7b, prevents incorrectly oriented insertion/interchanging; the bone separation-tool guide portion 8 is specifically attached to the respective side part 7a, 7b in the desired position with a form-fit.

In connection with FIG. 36, it can be seen that instead of the markings chosen in the first embodiment, which have the directional letters L and R, numerical and color markings are provided on the main and side parts 4; 7a, 7b in this second embodiment. The main part 4 is here marked with the number '1'. On the side facing the first side part 7a, the main part 4 is marked in blue, on the side facing the second side part 7b in green. The first side part 7a is in turn marked blue and is marked with the number '2' on its side facing the main part 4. On a side facing away from the main part 4, the first side part 7a is marked with the number '3'. The movable bone separation-tool guide portion 8 of the first side part 7a, located on the side facing away from main part 4, is also marked with the number '3' and the color blue. The second side part 7b is in turn marked green. Furthermore, the second side part 7b is marked with the number '2' on a side facing the main part 4 and with the number '3' on a side facing away from the main part 4. The movable bone separation-tool guide portion 8 of the second side part 7b, located on the side facing away from the main part 4, is also marked with the number '3' and the color green. The color markings are each formed as colored dots. The numbers are preferably engraved on the surface by means of a laser beam process.

Finally, FIG. 37 (in the removal position) and FIG. 48 (in the implantation position) show the respective receiving pockets 10a, 10b, 11a, 11b inserted in the respective main and side parts 4; 7a, 7b. The support crosspieces 13, 14 adjacent to the receiving pockets 10a, 10b, 11a, 11b are also particularly easy to identify. In this context, it is also apparent that the respective side part 7a, 7b is provided with more than two, namely three, first through holes 16. The first three through holes 16 of the first side part 7a are again lined up along the imaginary (second) connection line 18. In connection with FIG. 46, the intended reception of the implants 9 in the form of the bone plates in the receiving pockets 10a, 10b, 11a, 11b can be seen particularly well. The L-shaped FIGS. 84 are added to show how the sides of the support crosspieces 13, 14 are at least L-shaped in order to form the receiving pockets 10a, 10b, 11a, 11b.

In connection with FIGS. 38 to 40, 42 to 44, 49 and 52 it should be noted that the individual side parts 7a, 7b and the main part 4 can also be used independently of each other. Thus, main part 4 means any part that can in principle be used alone, next to another part (e.g. next to the first side part 7a or the second side part 7b) or next to, preferably in the middle of, two other parts (e.g. the first side part 7a and the second side part 7b). Each of the side parts 7a, 7b is also designed and usable as a separate part/main part in the sense of the claimed subject matter.

In connection with FIG. 51, it is illustrated that special milled parts 51 are also provided on the bracket seatings 19 for guiding the bone separation-tool guide portions 8/the bars 27, which are matched in form so that they cannot be incorrectly inserted/interchanged.

FIGS. 53 to 59 illustrate a third embodiment of the fibula bone-material removal and transfer template according to the invention. This third embodiment is again largely constructed according to the first embodiment, so that only the differences between these two embodiments are described below for the sake of simplicity.

As can be seen in this embodiment, the geometry of the respective side part 7a, 7b is different for insertion on main part 4. The main part 4, which can easily be seen in FIG. 59 alone, therefore has two differently designed receiving hookss 46a, 46b. A first receiving hooks 46a is formed on an end 35 of main part 4 facing the first side part 7a. A second receiving hooks 46b is formed on an end 35 facing the second side part 7b. Both receiving hookss 46a and 46b are essentially L-shaped in plan view. The first receiving hooks 46a has a different extension than the second receiving hooks 46b. In particular, a free end section of the L-shaped first receiving hooks 46a is longer than the free end section of the other second receiving hooks 46. The respective side parts 7a and 7b have hook receiving openings 47a, 47b corresponding to the respective receiving hookss 46a and 46b. The receiving pockets 10a, 10b, 11a, 11b, which are also implemented in this embodiment, are not shown further here for the sake of clarity.

In addition, an elongated hole 48 (e.g. shown in FIG. 59) is provided on a nose protruding from the main part 4, in order to be able to fix the template 1 to the lower jaw more easily.

LIST OF REFERENCE SIGNS 1 template
2 first support region
3 first bone region
4 main part
5 second support region
6 second bone region
7a first side part
7b second side part
8 bone separation-tool guide portion
9 implant
10a first receiving pocket of the main part
10b second receiving pocket of the main part
11a receiving pocket of the first side part
11b receiving pocket of the second side part
12 insertion opening
13 support crosspiece of the main part
14 support crosspiece of the side part
15 fixation means
16 first through hole
17 first connection line
18 second connection line
19 bracket seating
20 removal-aid bracket
21a first seating space
21b second seating space
22 implanting-aid bracket
23 stop region
24 third bone region
25 guide slit 26 vertical surface
27 bar
28 guide portion
29 receiving hole
30 clamp
31 spring portion
32 second through hole
33 lower jaw bone
34 fibula bone
35 end
36 base body
37 elevation
38 shifting mechanism
39 guide crosspiece
40 front side
41 grating
42 adjustment screw
43 fixation means
44 plate hole
45 fixation screw
46a first receiving hook
46b second receiving hook
47a first hook receiving opening
47b second hook receiving opening
48 elongated hole
49 pin
50 groove
51 milled part

The invention claimed is:

1. A fibula bone-material removal and transfer template having a plate-shaped and curved main part designed for application to a bone region, wherein at least one bone separation-tool guide portion can be or is removably attached to the main part, and wherein a receiving pocket designed to receive an implant is formed in the main part, wherein the main part has an at least L-shaped support crosspiece whose height directly determines the height of the receiving pocket.

2. The fibula bone-material removal and transfer template according to claim 1, wherein the main part has a first support region for application to a first bone region and that a side part which can be arranged or is arranged to the side of the main part and has a second support region for application to a second bone region is provided next to the main part.

3. The fibula bone-material removal and transfer template according to claims 2, wherein the first support region of the main part has the support crosspiece whose height directly determines the height of the receiving pocket of the main part.

4. The fibula bone-material removal and transfer template according to claims 2, wherein the second support region of the side part has a support crosspiece, the height of which directly determines the height of the receiving pocket of the side part.

5. The fibula bone-material removal and transfer template according to claims 2, wherein at least one through hole opening into the receiving pocket of the main part and penetrating the main part is provided in the main part for receiving a fixation means.

6. The fibula bone-material removal and transfer template according to claims 2, wherein at least one through hole opening into the receiving pocket of the side part and penetrating the side part is provided in the side part for receiving a fixation means.

7. The fibula bone-material removal and transfer template according to claim 2, wherein in the main part and/or the side part a bracket seating is provided, into which an aid bracket can be or is inserted.

8. The fibula bone-material removal and transfer template according to claims 2, wherein a second receiving pocket for receiving an implant is formed in the main part and wherein the support crosspiece separates the receiving pocket from the second receiving pocket and wherein the height of the support crosspiece directly determines the height of the second receiving pocket.

9. An assembly kit comprising a fibula bone-material removal and transfer template according to claim 1 and an implant which is dimensioned in such a way that it can be inserted into a seating space formed by the receiving pocket.

10. A method for modelling a lower jaw bone from a fibula with the following steps:
a) application of the fibula bone-material removal and transfer template having a plate-shaped and curved main part designed for application to a bone region, wherein at least one bone separation-tool guide portion can be or is removably attached to the main part, and wherein a receiving pocket designed to receive an implant is formed in the main part, wherein the main part has a support crosspiece whose height directly determines the height of the receiving pocket with at least the main part and/or a side part on a first bone region of the fibula and optionally with the side part on a second bone region of the fibula,
b) cutting the fibula by means of a bone separation tool guided along the at least one bone separation-tool guide portion in such a way that the two bone regions are separated from each other,
c) repositioning of the two separate bone regions in such a way that they are brought into contact and/or into a specific relative position to each other,
d) inserting an implant designed to connect the two bone regions into the receiving pocket of the main part and/or into the receiving pocket of the side part, and
e) fixing the implant by fixation means to the two bone regions under support of the implant at the main part and/or the side part.

* * * * *